(12) United States Patent  
Koo et al.

(10) Patent No.: US 9,272,359 B2
(45) Date of Patent: Mar. 1, 2016

(54) LIQUID-GAS INTERFACE PLASMA DEVICE

(75) Inventors: Il-Gyo Koo, Fort Collins, CO (US); George J. Collins, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 1022 days.

(21) Appl. No.: 13/637,331

(22) PCT Filed: Mar. 31, 2010

(86) PCT No.: PCT/US2010/029478
§ 371 (c)(1),
(2), (4) Date: Nov. 15, 2012

(87) PCT Pub. No.: WO2011/123124
PCT Pub. Date: Oct. 6, 2011

(65) Prior Publication Data
US 2013/0062014 A1  Mar. 14, 2013

Related U.S. Application Data

(63) Continuation of application No. PCT/US2009/045708, filed on May 29, 2009.

(60) Provisional application No. 61/057,667, filed on May 30, 2008.

(51) Int. Cl.
*A61L 2/00* (2006.01)
*H01J 7/24* (2006.01)
(Continued)

(52) U.S. Cl.
CPC ............... *B23K 10/00* (2013.01); *A61C 19/00* (2013.01); *A61C 19/066* (2013.01);
(Continued)

(58) Field of Classification Search
CPC ........ A61C 19/00; A61C 19/066; H05H 1/42; H05H 1/24; H05H 1/2443
USPC ........................................................ 422/22
See application file for complete search history.

(56) References Cited

U.S. PATENT DOCUMENTS

| 438,257 | A | 10/1890 | Raquet |
| 2,213,820 | A | 9/1940 | Maxson |

(Continued)

FOREIGN PATENT DOCUMENTS

| DE | 3710489 | 11/1987 |
| DE | 4139029 | 6/1993 |

(Continued)

OTHER PUBLICATIONS

English translation JP 2003-093869, Takuya, Apr. 2003.*

(Continued)

*Primary Examiner* — Keath Chen

(57) ABSTRACT

A plasma system for treating a workpiece is disclosed. The plasma system includes: a plasma device including an electrode formed from a metal alloy and a dielectric layer covering the electrode, the dielectric layer including a distal portion extending distally past a distal end of the electrode by a predetermined distance; a liquid source configured to supply a liquid to a workpiece; an ionizable media source coupled to the plasma device and configured to supply ionizable media thereto; and a power source coupled to the electrode and configured to ignite the ionizable media at the plasma device to form a plasma effluent in the presence of the liquid, whereby the plasma effluent reacts with the liquid to form at least one reactive species that interacts with the workpiece.

6 Claims, 11 Drawing Sheets

(51) Int. Cl.

| | |
|---|---|
| *H05B 31/26* | (2006.01) |
| *B23K 10/00* | (2006.01) |
| *A61C 19/00* | (2006.01) |
| *A61C 19/06* | (2006.01) |
| *H05H 1/42* | (2006.01) |
| *H05H 1/24* | (2006.01) |

(52) U.S. Cl.
CPC .............. H05H 1/2406 (2013.01); H05H 1/42 (2013.01); *H05H 2001/2418* (2013.01); *H05H 2001/2431* (2013.01); *H05H 2001/2443* (2013.01)

(56) References Cited

U.S. PATENT DOCUMENTS

| | | | |
|---|---|---|---|
| 2,598,301 | A | 5/1952 | Rajchman |
| 3,134,947 | A | 5/1964 | Charasz |
| 3,434,476 | A | 3/1969 | Shaw et al. |
| 3,671,195 | A | 6/1972 | Bersin |
| 3,838,242 | A | 9/1974 | Goucher |
| 3,903,891 | A | 9/1975 | Brayshaw |
| 3,938,525 | A | 2/1976 | Coucher |
| 3,991,764 | A | 11/1976 | Incropera et al. |
| 4,010,400 | A | 3/1977 | Hollister |
| 4,017,707 | A | 4/1977 | Brown et al. |
| 4,143,337 | A | 3/1979 | Beaulieu |
| 4,177,422 | A | 12/1979 | Deficis et al. |
| 4,181,897 | A | 1/1980 | Miller |
| 4,188,426 | A | 2/1980 | Auerbach |
| 4,274,919 | A | 6/1981 | Jensen et al. |
| 4,337,415 | A | 6/1982 | Dürr |
| 4,466,824 | A * | 8/1984 | Gauvin et al. .................. 373/22 |
| 4,577,165 | A | 3/1986 | Uehara et al. |
| 4,629,887 | A | 12/1986 | Bernier |
| 4,629,940 | A | 12/1986 | Gagne et al. |
| 4,780,803 | A | 10/1988 | Dede Garcia-Santamaria |
| 4,781,175 | A | 11/1988 | McGreevy et al. |
| 4,818,916 | A | 4/1989 | Morrisroe |
| 4,877,999 | A | 10/1989 | Knapp et al. |
| 4,901,719 | A | 2/1990 | Trenconsky et al. |
| 4,922,210 | A | 5/1990 | Flachenecker et al. |
| 4,956,582 | A | 9/1990 | Bourassa |
| 5,025,373 | A | 6/1991 | Keyser, Jr. et al. |
| 5,041,110 | A | 8/1991 | Fleenor |
| 5,088,997 | A | 2/1992 | Delahuerga et al. |
| 5,098,430 | A | 3/1992 | Fleenor |
| 5,117,088 | A | 5/1992 | Stava |
| 5,124,526 | A | 6/1992 | Muller et al. |
| 5,135,604 | A | 8/1992 | Kumar et al. |
| 5,155,547 | A | 10/1992 | Casper et al. |
| 5,159,173 | A | 10/1992 | Frind et al. |
| 5,180,949 | A | 1/1993 | Durr |
| 5,217,457 | A | 6/1993 | Delahuerga et al. |
| 5,223,457 | A | 6/1993 | Mintz et al. |
| 5,256,138 | A | 10/1993 | Burek et al. |
| 5,280,154 | A | 1/1994 | Cuomo et al. |
| 5,300,068 | A | 4/1994 | Rosar et al. |
| 5,304,279 | A | 4/1994 | Coultas et al. |
| 5,320,621 | A | 6/1994 | Gordon et al. |
| 5,334,834 | A | 8/1994 | Ito et al. |
| RE34,780 | E | 11/1994 | Trenconsky et al. |
| 5,383,019 | A | 1/1995 | Farrell et al. |
| 5,384,167 | A | 1/1995 | Nishiwaki et al. |
| 5,401,350 | A | 3/1995 | Patrick et al. |
| 5,449,356 | A | 9/1995 | Walbrink et al. |
| 5,449,432 | A | 9/1995 | Hanawa |
| 5,505,729 | A | 4/1996 | Rau |
| 5,526,138 | A | 6/1996 | Sato |
| 5,534,231 | A | 7/1996 | Savas |
| 5,554,172 | A | 9/1996 | Horner et al. |
| 5,607,509 | A | 3/1997 | Schumacher et al. |
| 5,618,382 | A | 4/1997 | Mintz et al. |
| 5,656,186 | A | 8/1997 | Mourou et al. |
| 5,669,904 | A | 9/1997 | Platt, Jr. et al. |
| 5,669,907 | A | 9/1997 | Plat, Jr. et al. |
| 5,683,366 | A * | 11/1997 | Eggers et al. .................. 604/114 |
| 5,688,357 | A | 11/1997 | Hanawa |
| 5,697,882 | A | 12/1997 | Eggers et al. |
| 5,707,402 | A | 1/1998 | Heim |
| 5,708,330 | A | 1/1998 | Rothenbuhler et al. |
| 5,720,745 | A | 2/1998 | Farin et al. |
| 5,733,511 | A | 3/1998 | De Francesco |
| 5,810,764 | A | 9/1998 | Eggers et al. |
| 5,818,581 | A | 10/1998 | Kurosawa et al. |
| 5,841,531 | A | 11/1998 | Gliddon |
| 5,843,019 | A | 12/1998 | Eggers et al. |
| 5,843,079 | A | 12/1998 | Suslov |
| 5,845,488 | A | 12/1998 | Hancock et al. |
| 5,849,136 | A | 12/1998 | Mintz et al. |
| 5,858,477 | A | 1/1999 | Veerasamy et al. |
| 5,865,937 | A | 2/1999 | Shan et al. |
| 5,866,985 | A | 2/1999 | Coultas et al. |
| 5,892,328 | A | 4/1999 | Shang et al. |
| 5,909,086 | A | 6/1999 | Kim et al. |
| 5,961,772 | A | 10/1999 | Selwyn |
| 5,977,715 | A | 11/1999 | Li et al. |
| 6,013,075 | A | 1/2000 | Avramenko et al. |
| 6,020,794 | A | 2/2000 | Wilbur |
| 6,024,733 | A | 2/2000 | Eggers et al. |
| 6,027,601 | A | 2/2000 | Hanawa |
| 6,030,667 | A | 2/2000 | Nakagawa et al. |
| 6,033,582 | A | 3/2000 | Lee et al. |
| 6,036,878 | A | 3/2000 | Collins |
| 6,046,546 | A | 4/2000 | Porter et al. |
| 6,047,700 | A | 4/2000 | Eggers et al. |
| 6,053,172 | A | 4/2000 | Hovda et al. |
| 6,063,079 | A | 5/2000 | Hovda et al. |
| 6,063,084 | A | 5/2000 | Farin |
| 6,063,937 | A | 5/2000 | Dlubala et al. |
| 6,066,134 | A | 5/2000 | Eggers et al. |
| 6,086,585 | A | 7/2000 | Hovda et al. |
| 6,099,523 | A | 8/2000 | Kim et al. |
| 6,102,046 | A | 8/2000 | Weinstein et al. |
| 6,105,581 | A | 8/2000 | Eggers et al. |
| 6,109,268 | A | 8/2000 | Thapliyal et al. |
| 6,110,395 | A | 8/2000 | Gibson, Jr. |
| 6,113,597 | A | 9/2000 | Eggers et al. |
| 6,132,575 | A | 10/2000 | Pandumsoporn et al. |
| 6,137,237 | A | 10/2000 | MacLennan et al. |
| 6,142,992 | A | 11/2000 | Cheng et al. |
| 6,149,620 | A | 11/2000 | Baker et al. |
| 6,153,852 | A | 11/2000 | Blutke et al. |
| 6,159,208 | A | 12/2000 | Hovda et al. |
| 6,159,531 | A | 12/2000 | Dang et al. |
| 6,170,428 | B1 | 1/2001 | Redeker et al. |
| 6,172,130 | B1 | 1/2001 | Bellesort |
| 6,178,918 | B1 | 1/2001 | Van Os et al. |
| 6,179,836 | B1 | 1/2001 | Eggers et al. |
| 6,182,469 | B1 | 2/2001 | Campbell et al. |
| 6,183,655 | B1 | 2/2001 | Wang et al. |
| 6,190,381 | B1 | 2/2001 | Olsen et al. |
| 6,197,026 | B1 | 3/2001 | Farin et al. |
| 6,203,542 | B1 | 3/2001 | Ellsberry et al. |
| 6,206,871 | B1 | 3/2001 | Zanon et al. |
| 6,206,878 | B1 | 3/2001 | Bishop et al. |
| 6,207,924 | B1 | 3/2001 | Trassy |
| 6,210,402 | B1 | 4/2001 | Olsen et al. |
| 6,210,410 | B1 | 4/2001 | Farin et al. |
| 6,213,999 | B1 | 4/2001 | Platt, Jr. et al. |
| 6,222,186 | B1 | 4/2001 | Li et al. |
| 6,224,592 | B1 | 5/2001 | Eggers et al. |
| 6,225,593 | B1 | 5/2001 | Howieson et al. |
| 6,228,078 | B1 | 5/2001 | Eggers et al. |
| 6,228,082 | B1 | 5/2001 | Baker et al. |
| 6,228,229 | B1 | 5/2001 | Raaijmakers et al. |
| 6,235,020 | B1 | 5/2001 | Cheng et al. |
| 6,237,526 | B1 | 5/2001 | Brcka |
| 6,238,391 | B1 | 5/2001 | Olsen et al. |
| 6,242,735 | B1 | 6/2001 | Li et al. |
| 6,248,250 | B1 | 6/2001 | Hanawa et al. |
| 6,252,354 | B1 | 6/2001 | Collins et al. |
| 6,254,600 | B1 | 7/2001 | Willink et al. |
| 6,254,738 | B1 | 7/2001 | Stimson et al. |

(56) References Cited

U.S. PATENT DOCUMENTS

| | | |
|---|---|---|
| 6,264,650 B1 | 7/2001 | Hovda et al. |
| 6,264,651 B1 | 7/2001 | Underwood et al. |
| 6,264,652 B1 | 7/2001 | Eggers et al. |
| 6,270,687 B1 | 8/2001 | Ye et al. |
| 6,277,112 B1 | 8/2001 | Underwood et al. |
| 6,277,251 B1 | 8/2001 | Hwang et al. |
| 6,283,961 B1 | 9/2001 | Underwood et al. |
| 6,287,980 B1 | 9/2001 | Hanazaki et al. |
| 6,291,938 B1 | 9/2001 | Jewett et al. |
| 6,296,636 B1 | 10/2001 | Cheng et al. |
| 6,296,638 B1 | 10/2001 | Davison et al. |
| 6,299,948 B1 | 10/2001 | Gherardi et al. |
| 6,309,387 B1 | 10/2001 | Eggers et al. |
| 6,313,587 B1 | 11/2001 | MacLennan et al. |
| 6,326,584 B1 | 12/2001 | Jewett et al. |
| 6,326,739 B1 | 12/2001 | MacLennan et al. |
| 6,328,760 B1 | 12/2001 | James |
| 6,329,757 B1 | 12/2001 | Morrisroe et al. |
| 6,333,481 B2 | 12/2001 | Augeraud et al. |
| 6,345,588 B1 | 2/2002 | Stimson |
| 6,346,108 B1 | 2/2002 | Fischer |
| 6,348,051 B1 | 2/2002 | Farin et al. |
| 6,353,206 B1 | 3/2002 | Roderick |
| 6,355,032 B1 | 3/2002 | Hovda et al. |
| 6,363,937 B1 | 4/2002 | Hovda et al. |
| 6,365,063 B2 | 4/2002 | Collins et al. |
| 6,375,750 B1 | 4/2002 | Van Os et al. |
| 6,379,351 B1 | 4/2002 | Thapliyal et al. |
| 6,387,088 B1 | 5/2002 | Shattuck et al. |
| 6,391,025 B1 | 5/2002 | Weinstein et al. |
| 6,396,214 B1 | 5/2002 | Grosse et al. |
| 6,401,652 B1 | 6/2002 | Mohn et al. |
| 6,402,517 B1 | 6/2002 | Hozumi et al. |
| 6,409,933 B1 | 6/2002 | Holland et al. |
| RE37,780 E | 7/2002 | Lanzani et al. |
| 6,416,507 B1 | 7/2002 | Eggers et al. |
| 6,416,508 B1 | 7/2002 | Eggers et al. |
| 6,416,633 B1 | 7/2002 | Spence |
| 6,424,099 B1 | 7/2002 | Kirkpatrick et al. |
| 6,424,232 B1 | 7/2002 | Mavretic et al. |
| 6,432,103 B1 | 8/2002 | Ellsberry et al. |
| 6,432,260 B1 | 8/2002 | Mahoney et al. |
| 6,443,948 B1 | 9/2002 | Suslov |
| 6,444,084 B1 | 9/2002 | Collins |
| 6,445,141 B1 | 9/2002 | Kastner et al. |
| 6,459,066 B1 | 10/2002 | Khater et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,464,889 B1 | 10/2002 | Lee et al. |
| 6,464,891 B1 | 10/2002 | Druz et al. |
| 6,468,270 B1 | 10/2002 | Hovda et al. |
| 6,468,274 B1 | 10/2002 | Alleyne et al. |
| 6,471,822 B1 | 10/2002 | Yin et al. |
| 6,474,258 B2 | 11/2002 | Brcka |
| 6,475,217 B1 | 11/2002 | Platt |
| 6,482,201 B1 | 11/2002 | Olsen et al. |
| 6,497,826 B2 | 12/2002 | Li et al. |
| 6,500,173 B2 | 12/2002 | Underwood et al. |
| 6,502,416 B2 | 1/2003 | Kawasumi et al. |
| 6,502,588 B2 | 1/2003 | Li et al. |
| 6,507,155 B1 | 1/2003 | Barnes et al. |
| 6,508,982 B1 * | 1/2003 | Shoji ............................ 422/22 |
| 6,525,481 B1 | 2/2003 | Klima et al. |
| 6,534,133 B1 | 3/2003 | Kaloyeros et al. |
| 6,540,741 B1 | 4/2003 | Underwood et al. |
| 6,544,261 B2 | 4/2003 | Ellsberry et al. |
| 6,558,383 B2 | 5/2003 | Cunningham et al. |
| 6,575,968 B1 | 6/2003 | Eggers et al. |
| 6,579,289 B2 | 6/2003 | Schnitzler |
| 6,579,426 B1 | 6/2003 | Van Gogh et al. |
| 6,582,423 B1 | 6/2003 | Thapliyal et al. |
| 6,582,427 B1 | 6/2003 | Goble et al. |
| 6,582,429 B2 | 6/2003 | Krishnan et al. |
| 6,589,237 B2 | 7/2003 | Woloszko et al. |
| 6,589,437 B1 | 7/2003 | Collins |
| 6,595,990 B1 | 7/2003 | Weinstein et al. |
| 6,617,794 B2 | 9/2003 | Barnes et al. |
| 6,624,583 B1 | 9/2003 | Coll et al. |
| 6,625,555 B2 | 9/2003 | Kuan et al. |
| 6,629,974 B2 | 10/2003 | Penny et al. |
| 6,632,193 B1 | 10/2003 | Davison et al. |
| 6,632,220 B1 | 10/2003 | Eggers et al. |
| 6,642,526 B2 | 11/2003 | Hartley |
| 6,646,386 B1 | 11/2003 | Sirkis et al. |
| 6,652,717 B1 | 11/2003 | Hong |
| 6,653,594 B2 | 11/2003 | Nakamura et al. |
| 6,657,594 B2 | 12/2003 | Anderson |
| 6,659,106 B1 | 12/2003 | Hovda et al. |
| 6,663,017 B2 | 12/2003 | Endres et al. |
| 6,666,865 B2 | 12/2003 | Platt |
| 6,685,803 B2 | 2/2004 | Lazarovich et al. |
| 6,712,811 B2 | 3/2004 | Underwood et al. |
| 6,719,754 B2 | 4/2004 | Underwood et al. |
| 6,719,883 B2 | 4/2004 | Stimson |
| 6,723,091 B2 | 4/2004 | Goble et al. |
| 6,726,684 B1 | 4/2004 | Woloszko et al. |
| 6,740,842 B2 | 5/2004 | Johnson et al. |
| 6,746,447 B2 | 6/2004 | Davison et al. |
| 6,763,836 B2 | 7/2004 | Tasto et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,774,569 B2 | 8/2004 | De Vries et al. |
| 6,780,178 B2 | 8/2004 | Palanker et al. |
| 6,780,184 B2 | 8/2004 | Tanrisever |
| 6,781,317 B1 | 8/2004 | Goodman |
| 6,787,730 B2 | 9/2004 | Coccio et al. |
| 6,805,130 B2 | 10/2004 | Tasto et al. |
| 6,806,438 B2 | 10/2004 | Nakano et al. |
| 6,815,633 B1 | 11/2004 | Chen et al. |
| 6,818,140 B2 | 11/2004 | Ding |
| 6,832,996 B2 | 12/2004 | Woloszko et al. |
| 6,837,884 B2 | 1/2005 | Woloszko |
| 6,837,887 B2 | 1/2005 | Woloszko et al. |
| 6,837,888 B2 | 1/2005 | Ciarrocca et al. |
| 6,840,937 B2 | 1/2005 | Van Wyk |
| 6,849,191 B2 | 2/2005 | Ono et al. |
| 6,852,112 B2 | 2/2005 | Platt |
| 6,855,143 B2 | 2/2005 | Davison et al. |
| 6,855,225 B1 | 2/2005 | Su et al. |
| 6,861,377 B1 | 3/2005 | Hirai et al. |
| 6,867,859 B1 | 3/2005 | Powell |
| 6,876,155 B2 | 4/2005 | Howald et al. |
| 6,890,332 B2 | 5/2005 | Truckai et al. |
| 6,896,672 B1 | 5/2005 | Eggers et al. |
| 6,896,674 B1 | 5/2005 | Woloszko et al. |
| 6,896,775 B2 | 5/2005 | Chistyakov |
| 6,909,237 B1 | 6/2005 | Park et al. |
| 6,911,029 B2 | 6/2005 | Platt |
| 6,915,806 B2 | 7/2005 | Pacek et al. |
| 6,919,527 B2 | 7/2005 | Boulos et al. |
| 6,920,883 B2 | 7/2005 | Bessette et al. |
| 6,921,398 B2 | 7/2005 | Carmel et al. |
| 6,922,093 B2 | 7/2005 | Kanda |
| 6,924,455 B1 | 8/2005 | Chen et al. |
| 6,929,640 B1 | 8/2005 | Underwood et al. |
| 6,949,096 B2 | 9/2005 | Davison et al. |
| 6,949,887 B2 | 9/2005 | Kirkpatrick et al. |
| 6,958,063 B1 | 10/2005 | Soll et al. |
| 6,974,453 B2 | 12/2005 | Woloszko et al. |
| 6,991,631 B2 | 1/2006 | Woloszko et al. |
| 7,004,941 B2 | 2/2006 | Tvinnereim et al. |
| 7,019,253 B2 | 3/2006 | Johnson et al. |
| 7,046,088 B2 | 5/2006 | Ziegler |
| 7,048,733 B2 | 5/2006 | Hartley et al. |
| 7,070,596 B1 | 7/2006 | Woloszko et al. |
| 7,084,832 B2 | 8/2006 | Pribyl |
| 7,090,672 B2 | 8/2006 | Underwood et al. |
| 7,096,819 B2 | 8/2006 | Chen et al. |
| 7,100,532 B2 | 9/2006 | Pribyl |
| 7,104,986 B2 | 9/2006 | Hovda et al. |
| 7,115,185 B1 | 10/2006 | Gonzalez et al. |
| 7,122,035 B2 | 10/2006 | Canady |

(56) References Cited

U.S. PATENT DOCUMENTS

| | | |
|---|---|---|
| 7,122,965 B2 | 10/2006 | Goodman |
| 7,131,969 B1 | 11/2006 | Hovda et al. |
| 7,132,620 B2 | 11/2006 | Coelho et al. |
| 7,132,996 B2 | 11/2006 | Evans et al. |
| 7,150,745 B2 | 12/2006 | Stern et al. |
| 7,157,857 B2 | 1/2007 | Brouk et al. |
| 7,160,521 B2 | 1/2007 | Porshnev et al. |
| 7,161,112 B2 | 1/2007 | Smith et al. |
| 7,164,484 B2 | 1/2007 | Takahashi et al. |
| 7,165,451 B1 | 1/2007 | Brooks et al. |
| 7,166,816 B1 | 1/2007 | Chen et al. |
| 7,179,255 B2 | 2/2007 | Lettice et al. |
| 7,186,234 B2 | 3/2007 | Dahla et al. |
| 7,189,939 B2 | 3/2007 | Lee et al. |
| 7,189,940 B2 | 3/2007 | Kumar et al. |
| 7,192,428 B2 | 3/2007 | Eggers et al. |
| 7,199,399 B2 | 4/2007 | Chin-Lung et al. |
| 7,201,750 B1 | 4/2007 | Eggers et al. |
| 7,214,280 B2 | 5/2007 | Kumar et al. |
| 7,214,934 B2 | 5/2007 | Stevenson |
| 7,217,268 B2 | 5/2007 | Eggers et al. |
| 7,217,903 B2 | 5/2007 | Bayer et al. |
| 7,220,261 B2 | 5/2007 | Truckai et al. |
| 7,227,097 B2 | 6/2007 | Kumar et al. |
| 7,238,185 B2 | 7/2007 | Palanker et al. |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,271,363 B2 | 9/2007 | Lee et al. |
| 7,275,344 B2 | 10/2007 | Woodmansee, III et al. |
| 7,276,063 B2 | 10/2007 | Davison et al. |
| 7,282,244 B2 | 10/2007 | Schaepkens et al. |
| 7,292,191 B2 | 11/2007 | Anderson |
| 7,297,143 B2 | 11/2007 | Woloszko et al. |
| 7,297,145 B2 | 11/2007 | Woloszko et al. |
| 7,298,091 B2 | 11/2007 | Pickard et al. |
| 7,309,843 B2 | 12/2007 | Kumar et al. |
| 7,311,708 B2 | 12/2007 | McClurken |
| 7,316,682 B2 | 1/2008 | Konesky |
| 7,318,823 B2 | 1/2008 | Sharps et al. |
| 7,331,957 B2 | 2/2008 | Woloszko et al. |
| 7,353,771 B2 | 4/2008 | Millner et al. |
| 7,355,379 B2 | 4/2008 | Kitamura et al. |
| 7,357,798 B2 | 4/2008 | Sharps et al. |
| 7,361,175 B2 | 4/2008 | Suslov |
| 7,382,129 B2 | 6/2008 | Mills |
| 7,387,625 B2 | 6/2008 | Hovda et al. |
| 7,393,351 B2 | 7/2008 | Woloszko et al. |
| 7,399,944 B2 | 7/2008 | DeVries et al. |
| 7,410,669 B2 | 8/2008 | Dieckhoff et al. |
| 7,419,488 B2 | 9/2008 | Ciarrocca et al. |
| 7,426,900 B2 | 9/2008 | Brcka |
| 7,429,260 B2 | 9/2008 | Underwood et al. |
| 7,429,262 B2 | 9/2008 | Woloszko et al. |
| 7,431,857 B2 | 10/2008 | Shannon et al. |
| 7,435,247 B2 | 10/2008 | Woloszko et al. |
| 7,442,191 B2 | 10/2008 | Hovda et al. |
| 7,445,619 B2 | 11/2008 | Auge, II et al. |
| 7,449,021 B2 | 11/2008 | Underwood et al. |
| 7,453,403 B2 | 11/2008 | Anderson |
| 7,458,973 B2 | 12/2008 | Ouchi |
| 7,459,899 B2 | 12/2008 | Mattaboni et al. |
| 7,468,059 B2 | 12/2008 | Eggers et al. |
| 7,480,299 B2 | 1/2009 | O'Keeffe et al. |
| 7,489,206 B2 | 2/2009 | Kotani et al. |
| 7,491,200 B2 | 2/2009 | Underwood |
| 7,497,119 B2 | 3/2009 | Brooks et al. |
| 7,498,000 B2 | 3/2009 | Pekshev et al. |
| 7,506,014 B2 | 3/2009 | Drummond |
| 7,507,236 B2 | 3/2009 | Eggers et al. |
| 7,510,665 B2 | 3/2009 | Shannon et al. |
| 7,511,246 B2 | 3/2009 | Morrisroe |
| 7,549,990 B2 | 6/2009 | Canady |
| 7,563,261 B2 | 7/2009 | Carmel et al. |
| 7,566,333 B2 | 7/2009 | Van Wyk et al. |
| 7,572,255 B2 | 8/2009 | Sartor et al. |
| 7,578,817 B2 | 8/2009 | Canady |
| 7,578,818 B2 | 8/2009 | Platt |
| 7,589,473 B2 | 9/2009 | Suslov |
| 7,601,150 B2 | 10/2009 | Farin |
| 7,608,839 B2 | 10/2009 | Coulombe et al. |
| 7,611,509 B2 | 11/2009 | Van Wyk |
| 7,628,787 B2 | 12/2009 | Sartor et al. |
| 7,632,267 B2 | 12/2009 | Dahla |
| 7,633,231 B2 | 12/2009 | Watson |
| 7,648,503 B2 | 1/2010 | Podhajsky |
| 7,666,478 B2 | 2/2010 | Paulussen et al. |
| 7,691,101 B2 | 4/2010 | Davison et al. |
| 7,691,102 B2 | 4/2010 | Podhajsky et al. |
| 7,708,733 B2 | 5/2010 | Sanders et al. |
| 7,715,889 B2 | 5/2010 | Ito |
| 7,758,575 B2 | 7/2010 | Beller |
| 7,824,398 B2 | 11/2010 | Woloszko et al. |
| 7,879,034 B2 | 2/2011 | Woloszko et al. |
| 7,887,891 B2 | 2/2011 | Rius |
| 7,892,223 B2 | 2/2011 | Geiselhart |
| 7,892,230 B2 | 2/2011 | Woloszko |
| 7,901,403 B2 | 3/2011 | Woloszko et al. |
| 7,940,008 B2 | 5/2011 | Mattaboni et al. |
| 7,949,407 B2 | 5/2011 | Kaplan et al. |
| 2001/0025177 A1 | 9/2001 | Woloszko et al. |
| 2001/0054601 A1 | 12/2001 | Ding |
| 2002/0014832 A1 | 2/2002 | Moradi et al. |
| 2002/0022836 A1 | 2/2002 | Goble et al. |
| 2002/0022838 A1 | 2/2002 | Cunningham et al. |
| 2002/0023899 A1 | 2/2002 | Khater et al. |
| 2002/0092826 A1 | 7/2002 | Ding |
| 2002/0122252 A1 | 9/2002 | Hebrink et al. |
| 2002/0125207 A1 | 9/2002 | Ono et al. |
| 2002/0132380 A1 | 9/2002 | Nakano et al. |
| 2002/0148734 A1 | 10/2002 | Bleck et al. |
| 2003/0006019 A1 | 1/2003 | Johnson et al. |
| 2003/0008327 A1 | 1/2003 | Ornatskaia |
| 2003/0027186 A1 | 2/2003 | Pierce |
| 2003/0036753 A1 | 2/2003 | Morgan et al. |
| 2003/0075522 A1 | 4/2003 | Weichart et al. |
| 2003/0093073 A1 | 5/2003 | Platt |
| 2003/0105456 A1 | 6/2003 | Lin |
| 2003/1018683 | 6/2003 | Wu |
| 2003/0132198 A1 | 7/2003 | Ono et al. |
| 2003/0158545 A1 | 8/2003 | Hovda et al. |
| 2003/0208194 A1 | 11/2003 | Hovda et al. |
| 2003/0228416 A1 | 12/2003 | Iwamaru |
| 2004/0007985 A1 | 1/2004 | De Vries et al. |
| 2004/0022669 A1* | 2/2004 | Ruan et al. ............ 422/22 |
| 2004/0027127 A1 | 2/2004 | Mills |
| 2004/0075375 A1 | 4/2004 | Miyashita et al. |
| 2004/0086434 A1 | 5/2004 | Gadgil et al. |
| 2004/0111219 A1 | 6/2004 | Gulati |
| 2004/0116918 A1 | 6/2004 | Konesky |
| 2004/0129212 A1 | 7/2004 | Gadgil et al. |
| 2004/0138658 A1 | 7/2004 | Farin et al. |
| 2004/0181220 A1 | 9/2004 | Farin |
| 2005/0015001 A1 | 1/2005 | Lec et al. |
| 2005/0017646 A1 | 1/2005 | Boulos et al. |
| 2005/0080413 A1 | 4/2005 | Canady |
| 2005/0103748 A1 | 5/2005 | Yamaguchi et al. |
| 2005/0107786 A1 | 5/2005 | Canady |
| 2005/0159317 A1* | 7/2005 | Wakamura ............ 504/367 |
| 2005/0205212 A1 | 9/2005 | Singh et al. |
| 2006/0004354 A1 | 1/2006 | Suslov |
| 2006/0011465 A1 | 1/2006 | Burke et al. |
| 2006/0017388 A1 | 1/2006 | Stevenson |
| 2006/0036239 A1 | 2/2006 | Canady |
| 2006/0038992 A1 | 2/2006 | Morrisroe |
| 2006/0052771 A1 | 3/2006 | Sartor et al. |
| 2006/0052772 A1 | 3/2006 | Sartor et al. |
| 2006/0065628 A1 | 3/2006 | Vahedi et al. |
| 2006/0127879 A1 | 6/2006 | Fuccione |
| 2006/0172429 A1 | 8/2006 | Nilsson et al. |
| 2006/0175015 A1 | 8/2006 | Chen et al. |
| 2006/0200122 A1 | 9/2006 | Sartor et al. |
| 2006/0224146 A1 | 10/2006 | Lin |

(56) References Cited

U.S. PATENT DOCUMENTS

| | | | |
|---|---|---|---|
| 2006/0266735 A1 | 11/2006 | Shannon et al. |
| 2006/0278254 A1 | 12/2006 | Jackson |
| 2007/0014752 A1 | 1/2007 | Roy et al. |
| 2007/0021747 A1 | 1/2007 | Suslov |
| 2007/0021748 A1 | 1/2007 | Suslov |
| 2007/0029292 A1 | 2/2007 | Suslov |
| 2007/0029500 A1 | 2/2007 | Coulombe et al. |
| 2007/0039389 A1 | 2/2007 | Brooks et al. |
| 2007/0068899 A1 | 3/2007 | Yoon |
| 2007/0084563 A1 | 4/2007 | Holland |
| 2007/0087455 A1 | 4/2007 | Hoffman |
| 2007/0149970 A1 | 6/2007 | Schnitzler et al. |
| 2007/0163499 A1 | 7/2007 | Finn et al. |
| 2007/0210035 A1 | 9/2007 | Twarog et al. |
| 2007/0213704 A1 | 9/2007 | Truckai et al. |
| 2007/0251920 A1 | 11/2007 | Hoffman |
| 2007/0255271 A1 | 11/2007 | Dabney et al. |
| 2007/0258329 A1 | 11/2007 | Winey |
| 2007/7291804 | 11/2007 | Suslov |
| 2007/0282322 A1 | 12/2007 | Dabney et al. |
| 2007/0282323 A1 | 12/2007 | Woloszko et al. |
| 2007/0292972 A1 | 12/2007 | Paulussen et al. |
| 2008/0023443 A1 | 1/2008 | Paterson et al. |
| 2008/0039832 A1 | 2/2008 | Palanker et al. |
| 2008/0050291 A1 | 2/2008 | Nagasawa |
| 2008/0083701 A1 | 4/2008 | Shao et al. |
| 2008/0099434 A1 | 5/2008 | Chandrachood et al. |
| 2008/0099435 A1 | 5/2008 | Grimbergen |
| 2008/0099436 A1 | 5/2008 | Grimbergen |
| 2008/0108985 A1 | 5/2008 | Konesky |
| 2008/0167398 A1 | 7/2008 | Patil et al. |
| 2008/0179290 A1 | 7/2008 | Collins et al. |
| 2008/0185366 A1 | 8/2008 | Suslov |
| 2008/0268172 A1 | 10/2008 | Fukuda et al. |
| 2008/0284506 A1 | 11/2008 | Messer |
| 2008/0292497 A1 | 11/2008 | Vangeneugden et al. |
| 2008/0296567 A1 | 12/2008 | Irving et al. |
| 2009/0004620 A1 | 1/2009 | Liu et al. |
| 2009/0039789 A1 | 2/2009 | Nikolay |
| 2009/0048594 A1 | 2/2009 | Sartor et al. |
| 2009/0054893 A1 | 2/2009 | Sartor et al. |
| 2009/0054896 A1 | 2/2009 | Fridman et al. |
| 2009/0064933 A1 | 3/2009 | Liu et al. |
| 2009/0076505 A1 | 3/2009 | Arts |
| 2009/0216226 A1 | 8/2009 | Davison et al. |
| 2009/0275941 A1 | 11/2009 | Sartor et al. |
| 2009/0306552 A1* | 12/2009 | Furuzono et al. ............... 601/2 |
| 2010/0016856 A1 | 1/2010 | Platt, Jr. |
| 2010/0042094 A1 | 2/2010 | Arts |
| 2010/0069902 A1 | 3/2010 | Sartor et al. |
| 2010/0089742 A1 | 4/2010 | Suslov |
| 2010/0114096 A1 | 5/2010 | Podhajsky |
| 2010/0130973 A1 | 5/2010 | Choi et al. |
| 2010/0209293 A1* | 8/2010 | Ikawa et al. ................. 422/22 |

FOREIGN PATENT DOCUMENTS

| | | | |
|---|---|---|---|
| DE | 4326037 | | 2/1995 |
| DE | 9117019 | | 4/1995 |
| DE | 19537897 | | 3/1997 |
| DE | 9117299 | | 4/2000 |
| DE | 19848784 | | 5/2000 |
| DE | 29724247 | | 8/2000 |
| DE | 19524645 | | 11/2002 |
| EP | 0016542 | A2 | 10/1980 |
| EP | 0016542 | B1 | 10/1980 |
| EP | 0 495 699 | | 7/1992 |
| EP | 0602764 | A1 | 6/1994 |
| EP | 0956827 | | 11/1999 |
| EP | 1174901 | A2 | 1/2002 |
| FR | 1340509 | | 9/1963 |
| JP | 61-159953 | | 7/1986 |
| JP | 62-130777 | | 6/1987 |
| JP | 03-149797 | | 6/1991 |
| JP | 8-243755 | | 9/1996 |
| JP | 2000286094 | A | 10/2000 |
| JP | 2001332399 | A | 11/2001 |
| JP | 2003093869 | A | 4/2003 |
| JP | 2005-522824 | A | 7/2005 |
| JP | 2005276618 | A | 10/2005 |
| JP | 2006114450 | A | 4/2006 |
| JP | 2006310101 | A | 11/2006 |
| JP | 2007188748 | A | 7/2007 |
| JP | 2007207540 | A | 8/2007 |
| JP | 2008041495 | A | 2/2008 |
| JP | 2008071656 | A | 3/2008 |
| JP | 2010-242857 | | 10/2010 |
| SU | 1438745 | | 11/1988 |
| WO | WO 99/01887 | | 1/1999 |
| WO | WO 99/36940 | | 7/1999 |
| WO | WO 01/39555 | A1 | 5/2001 |
| WO | 03/085693 | A1 | 10/2003 |
| WO | WO 2004/032176 | A1 | 4/2004 |
| WO | 2004094306 | A1 | 11/2004 |
| WO | WO 2006/116252 | A2 | 11/2006 |
| WO | WO 2009041049 | * | 4/2009 ............... H05H 1/24 |
| WO | WO 2009/080273 | | 7/2009 |
| WO | 2009/146432 | A1 | 12/2009 |
| WO | WO 2009/146439 | | 12/2009 |
| WO | 2010008062 | A1 | 1/2010 |

OTHER PUBLICATIONS

Extended European Search Report corresponding to European Application No. 09755793.8, dated Jul. 21, 2014; 8 pages.
Japanese Notice of Final Rejection and Denial of Entry of Amendment (with English translation), issued Apr. 2, 2015, corresponding to Japanese Patent Application No. 2012-513022; 10 total pages.
Extended European Search Report issued in Appl. No. 10849146.5 dated Sep. 9, 2013.
U.S. Appl. No. 08/383,162, filed Feb. 3, 1995, Lawrence K. Pacer.
U.S. Appl. No. 08/619,380, filed Mar. 21, 1996, Gene H. Arts.
U.S. Appl. No. 08/621,151, filed Mar. 21, 1996, Robert B. Stoddard.
U.S. Appl. No. 08/878,694, filed Jun. 19, 1997, Lawrence K Pacer.
U.S. Appl. No. 09/270,856, filed Mar. 17, 1999, Gene H. Arts.
U.S. Appl. No. 09/504,640, filed Feb. 16, 2000, James Steven Cunningham.
U.S. Appl. No. 09/666,312, filed Sep. 21, 2000, Robert C. Platt.
U.S. Appl. No. 12/791,100, filed Jun. 1, 2010, Kristin D. Johnson.
U.S. Appl. No. 12/845,842, filed Jul. 29, 2010, Kristin D. Johnson.
Hernandez et al., "A Controlled Study of the Argon Beam Coagultor for Partial Nephrectomy"; The Journal of Urology, vol. 143, May 1990 J. Urol. 143: pp. 1062-1065.
Ward et al., "A Significant New Contribution to Radical Head and Neck Surgery"; Arch Otolaryngology, Head and Neck Surg., vol. 115 pp. 921-923 (Aug. 1989).
Lieberman et al., "Capacitive Discharges", Principles of Plasma Discharges and Materials Processing, John Wiley & Son, Inc. (2005) pp. 387-460.
Moore et al., "Confined Geometry Interactions of Downstream RF-Excited Atmospheric Plasma Wires", IEEE Transactions on Plasma Science, 0093-3813, (2008) pp. 1-2.
Walsh et al., "Contrasting Characteristics of Pulsed and Sinusoidal Cold Atmospheric Plasma Jets", Applied Physics Letters, 88, 171501 (2006) pp. 1-3.
Cho et al., "Coplanar ac Discharges Between Cylindrical Electrodes With a Nanoporous Alumina Dielectric: Modular Dielectric Barrier Plasma Devices", IEEE Transactions on Plasma Science, vol. 33, No. 2, (Apr. 2005) pp. 378-379.
Xu et al., "DBD Plasma Jet in Atmospheric Pressure Argon", IEEE Transactions on Plasma Science, vol. 36, No. 4, (Aug. 2008), pp. 1352-1353.
Alfred Grill, "Electron Cyclotron Resonance Plasmas", Cold Plasma in Materials Fabrication, IEEE Press (1994) pp. 40-43.
Brand et al., "Electrosurgical Debulking of Ovarian Cancer: A New Technique Using the Argon Beam Coagulator"; Gynecologic Oncology 39 pp. 115-118 (1990).

(56) References Cited

OTHER PUBLICATIONS

Grund et al., "Endoscopic Argon Plasma . . . Flexible Endoscopy"; Endoscopic Surgery and Allied Technologies, No. 1, vol. 2, pp. 42-46 (Feb. 1994).
Waye et al., "Endoscopic Treatment Options"; Techniques in Therapeutic Endoscopy, pp. 1.7-1.15, (1987).
B.D. Cullity, "Introduction to Magnetic Materials", University of Notre Dame; Addison-Wesley Publishing Company, Reading MA., (1972) pp. 23-28.
Brian Chapman, "Matching Networks", Glow Discharge Processes, John Wiley & Sons Inc., NY, (1980) pp. 153-172.
Yin et al., "Miniaturization of Inductively Coupled Plasma Sources", IEEE Transactions on Plasma Science, vol. 27, No. 5, (Oct. 1999) pp. 1516-1524.
Park et al., "Nanoporous Anodic Alumina Film on Glass: Improving Transparency by an Ion-Drift Process", Electrochemical and Solid-State Letters, 8 (3) (2005), pp. D5-D7.
P.A. Tulle, "Off-Resonance Microwave-Created Plasmas", Plasma Physics, Pergamon Press (1973) vol. 15, pp. 971-976.
Lieberman et al., "Ohmic Heating", Principles of Plasma Discharges and Materials Processing, John Wiley & Son, Inc. (2005) pp. 97-98.
Lieberman et al., "Optical Actinometry", Principles of Plasma Discharges and Materials Processing, John Wiley & Son, Inc. (2005) pp. 277-279.
Cho et al., "Ozone Production by Nanoporous Dielectric Barrier Glow Discharge in Atmospheric Pressure Air", Applied Physics Letters, 92, 101504, (2008) pp. 1-3.
Lieberman et al., "Particle and Energy Balance in Discharges", Principles of Plasma Discharges and Materials Processing, John Wiley & Son, Inc. (2005) pp. 329-381.
Woloszko et al., "Plasma Characteristics of Repetitively-Pulsed Electrical Discharges in Saline Solutions Used for Surgical Procedures", IEEE Transactions of Plasma Science, vol. 30, No. 3, (Jun. 2002) pp. 1376-1383.
Stoffels et al., "Plasma Needle for In Vivo Medical Treatment: Recent Developments and Perspectives", Plasma Sources Science and Technology 15 (2006) pp. 169-180.
Schaper et al., "Plasma Production and Vapour Layer Production at a Pulse Power Electrode in Saline Solution:", (2008) www.escampig2008.csic.es/PosterSessions/100.
Akitsu et al., "Plasma Sterilization Using Glow Discharge at Atmospheric Pressure", Surface & Coatings Technology 193, (2005) pp. 29-34.
Koo et al., "Room-temperature Slot Microplasma in Atmospheric Pressure Air Between Cylindrical Electrodes With a Nanoporous Alumina Dielectric", Applied Physics Letters, 91, 041502 (2007) pp. 1-3.
Brian Chapman, "Secondary Electron Emission", Glow Discharge Processes, John Wiley & Sons Inc., NY, (1980) pp. 82-138.
Moore et al., "Sensitive, Nonintrusive, In-Situ Measurement of Temporally and Spatially Resolved Plasma Electric Fields", Physical Review Letters, vol. 52, No. 7, (Feb. 13, 1984) pp. 538-541.
Lieberman et al., "Sheaths", Principles of Plasma Discharges and Materials Processing, John Wiley & Son, Inc. (2005) pp. 11-14.
Farin et al., Technology of Argon Plasma . . . Endoscopic Applications; Endoscopic Surgery and Allied Technologies, No. 1, vol. 2, pp. 71-77 (Feb. 1994).
Lieberman et al., "The Collisionless Sheath", Principles of Plasma Discharges and Materials Processing, John Wiley & Son, Inc. (2005) pp. 167-206.
Gupta et al., "The Potential of Pulsed Underwater Streamer Discharges as a Disinfection Technique", IEEE Transactions on Plasma Science, vol. 36, No. 4, (Aug. 2008) pp. 1621-1632.
Mark H. Mellow, "The Role of Endoscopic Laser Therapy in Gastrointestinal Neoplasms"; Advanced Therapeutic Endoscopy, pp. 17-21, (1990).
Silverstein et al., "Thermal Coagulation Therapy for Upper Gastrointestinal Bleeding"; Advanced Therapeutic Endoscopy, pp. 79-84, 1990.
Sobolewski, Mark A., "Current and Voltage Measurements in the Gaseous Electronics Conference RF Reference Cell," *J. Res. Natl. Inst. Stand. Technol.*, vol. 100, No. 4, pp. 341-351 (1995).
European Search Report EP 01 10 2843.8, dated May 15, 2001.
European Search Report EP 05 00 2257, dated Jun. 1, 2005.
European Search Report EP 05 01 8087, dated Oct. 17, 2005.
European Search Report EP 06 01 9572 dated Nov. 21, 2006.
European Search Report EP 07 00 4356 dated Jul. 2, 2007.
European Search Report EP 07 00 4659 dated Feb. 19, 2008.
European Search Report EP 07 00 4659—partial dated May 24, 2007.
European Search Report EP 09 00 4975 dated Sep. 11, 2009.
European Search Report EP 09 01 0519 dated Nov. 16, 2009.
European Search Report EP 09 01 0520 dated Dec. 10, 2009.
European Search Report EP 09 01 5212.5 dated Apr. 1, 2010.
European Search Report EP 09 17 1599.5 dated Mar. 16, 2010.
European Search Report EP 09 17 1600.1 dated Jan. 26, 2010.
European Search Report EP 10 174107.2 dated Nov. 5, 2010.
European Search Report EP 10 180 912.7 dated Dec. 8, 2010.
European Search Report EP 10 186524.4 dated Feb. 18, 2011.
International Search Report PCT/US98/19284, dated Jan. 14, 1999.
European Search Report EP 11168420.5 dated Jan. 5, 2012.
European Search Report EP 08015839.7 dated Dec. 19, 2008.
International Search Report and Written Opinion from Int'l Appl. No. PCT/US2009/005398 mailed Apr. 5, 2010.
International Search Report and Written Opinion from Int'l Appl. No. PCT/US2009/005389 mailed Oct. 26, 2009.
Japanese Notice of Final Rejection and Denial of Entry of Amendment (with English translation), dated Jun. 2, 2015, corresponding to Japanese Patent Application No. 2013-502548; 15 total pages.
English translation of Japanese Notice of Reasons for Rejection, dated Feb. 18, 2014, corresponding to Japanese Patent Application No. 2013-502548; 6 pages.
English translation of Japanese Notice of Reasons for Rejection, dated Oct. 7, 2014, corresponding to Japanese Patent Application No. 2013-502548; 6 pages.
Australian Patent Examination Report No. 1, dated Apr. 17, 2014, corresponding to Australian Patent Application No. 2010349784; 3 pages.
European Communication dated Jun. 17, 2014, corresponding to European Patent Application No. 10849146.5; 6 pages.
European Communication dated Oct. 22, 2015, corresponding to European Patent Application No. 09755793.8; 9 pages.
European Communication/Examination Report dated Jul. 14, 2015, corresponding to European Patent Application No. 09 845 329.3; 8 pages.

* cited by examiner

L > 2mm    L < 2mm
3mm
FIG. 8A    FIG. 8B
3mm
FIG. 9

LIQUID-GAS INTERFACE PLASMA DEVICE

CROSS-REFERENCE TO RELATED APPLICATION

The present application claims the benefit of and priority to International Application No. PCT/US2010/029478 filed by Koo et al. on Mar. 31, 2010, which is a continuation and claims the benefit of and priority to International Application No. PCT/US2009/045708 filed by Moore et al. on May 29, 2009, which claims the benefit of and priority to U.S. Provisional Application Ser. No. 61/057,667 entitled "PLASMA-BASED CHEMICAL SOURCE DEVICE AND METHOD OF USE THEREOF" filed by Moore et al. on May 30, 2008, the entire contents of all of which are incorporated by reference herein.

BACKGROUND

1. Technical Field

The present disclosure relates to plasma devices and processes for surface processing and material removal or deposition. More particularly, the disclosure relates to an apparatus and method for generating and directing chemically reactive, plasma-generated species in a plasma device along with excited-state species (e.g., energetic photons) that are specific to the selected ingredients.

2. Background of Related Art

Electrical discharges in dense media, such as liquids and gases at or near atmospheric pressure, can, under appropriate conditions, result in plasma formation. Plasmas have the unique ability to create large amounts of chemical species, such as ions, radicals, electrons, excited-state (e.g., metastable) species, molecular fragments, photons, and the like. The plasma species may be generated in a variety of internal energy states or external kinetic energy distributions by tailoring plasma electron temperature and electron density. In addition, adjusting spatial, temporal and temperature properties of the plasma creates specific changes to the material being irradiated by the plasma species and associated photon fluxes. Plasmas are also capable of generating photons including energetic ultraviolet photons that have sufficient energy to initiate photochemical and photocatalytic reaction paths in biological and other materials that are irradiated by the plasma photons.

SUMMARY

Plasmas have broad applicability to provide alternative solutions to industrial, scientific and medical needs, especially workpiece surface processing at low temperature. Plasmas may be delivered to a workpiece, thereby affecting multiple changes in the properties of materials upon which the plasmas impinge. Plasmas have the unique ability to create large fluxes of radiation (e.g., ultraviolet), ions, photons, electrons and other excited-state (e.g., metastable) species which are suitable for performing material property changes with high spatial, material selectivity, and temporal control. Plasmas may also remove a distinct upper layer of a workpiece but have little or no effect on a separate underlayer of the workpiece or it may be used to selectively remove a particular tissue from a mixed tissue region or selectively remove a tissue with minimal effect to adjacent organs of different tissue type.

One suitable application of the unique chemical species is to drive non-equilibrium or selective chemical reactions at or within the workpiece to provide for selective removal of only certain types of materials. Such selective processes are especially sought in biological tissue processing (e.g., mixed or multi-layered tissue), which allows for cutting and removal of tissue at low temperatures with differential selectivity to underlayers and adjacent tissues. This is particularly useful for removal of biofilms, mixtures of fatty and muscle tissue, debridement of surface layers.

The plasma species are capable of modifying the chemical nature of tissue surfaces by breaking chemical bonds, substituting or replacing surface-terminating species (e.g., surface functionalization) through volatilization, gasification or dissolution of surface materials (e.g., etching). With proper techniques, material choices and conditions, one can remove one type of tissue entirely without affecting a nearby different type of tissue. Controlling plasma conditions and parameters (including S-parameters, V, I, $\Theta$, and the like) allows for the selection of a set of specific particles, which, in turn, allows for selection of chemical pathways for material removal or modification as well as selectivity of removal of desired tissue type. The present disclosure provides for a system and method for creating plasma under a broad range of conditions including tailored geometries, various plasma feedstock media, number and location of electrodes and electrical excitation parameters (e.g., voltage, current, phase, frequency, pulse condition, etc.).

The supply of electrical energy that ignites and sustains the plasma discharge is delivered through substantially conductive electrodes that are in contact with the ionizable media and other plasma feedstocks. The present disclosure also provides for methods and apparatus that utilize specific electrode structures that improve and enhance desirable aspects of plasma operation such as higher electron temperature and higher secondary emission. In particular, the present disclosure provides for porous media for controlled release of chemical reactants.

Controlling plasma conditions and parameters allows for selection of a set of specific particles, which, in turn, allows for selection of chemical pathways for material removal or modification as well as selectivity of removal of desired tissue type. The present disclosure also provides for a system and method for generating plasmas that operate at or near atmospheric pressure. The plasmas include electrons that drive reactions at material surfaces in concert with other plasma species. Electrons delivered to the material surface can initiate a variety of processes including bond scission, which enables volatilization in subsequent reactions. The electron-driven reactions act synergistically with associated fluxes to achieve removal rates of material greater than either of the reactions acting alone.

The present disclosure provides for a system and method for treating tissue in a liquid media. In particular, the present disclosure provides for a plasma device that generates a plasma within a liquid media. The liquid media provides for higher density radicals, cooler environment and more chemical reaction sites for the plasma generated therein. This results in an increased chemical reaction rate between the plasma and liquid media than the reaction rate between atmospheric gases and the plasma. Liquids can provide 1,000 times higher concentrations of ions than gases, which results in increased chemical kinetics at similar conditions (e.g., temperature, pressure). In addition, liquids can create selective chemical dissolution on a plasma-modified surface. Once tissue is modified by a plasma, the surface terminations of the tissue are more reactive toward the compounds in the liquid than unmodified portions of the tissue. The liquid media provides for increase solubility between a plasma-treated surface and a solvent and can, therefore, be used to control desired chemical reactions. Further, the liquid media can be used to remove the heat from the plasma and the tissue surface.

The present disclosure also provides for systems and methods for whitening teeth. Hydrogen peroxide ($H_2O_2$) is commonly used as a tooth-whitening agent. $H_2O_2$ is applied directly (e.g., pure liquid form) or produced via chemical reactions from other compounds (e.g., carbamide peroxide). Various light sources are utilized to expedite the whitening reactions (e.g., flash lamps, ultraviolet light sources, etc.). These methods require relatively high volume concentration of hydrogen peroxide to be effective, at least 10% by volume concentration or more (e.g., 35% by volume). Lower concentrations (e.g., 5% to about 10%) require extended treatment time. In addition, use of high levels of hydrogen peroxide raises patient safety concerns. High concentration of hydrogen peroxide results in increased tooth sensitivity, mucosal irritation, alteration of enamel surface, damage to soft tissue (e.g., gums) as well as carcinogenic risks.

The present disclosure provides for a system and method of whitening teeth without using an external bleaching agent (e.g., external source of hydrogen peroxide). The method involves submerging the teeth in deionized water (e.g., via irrigation) and inserting a plasma generation device having a dielectrically covered electrode into the water. The plasma device generates a plasma in the water which produces relatively low concentration of hydrogen peroxide, about 0.03% by volume (several hours of plasma exposure), thereby reducing the safety risks associated with conventional hydrogen peroxide bleaching methods.

A plasma system for treating a workpiece is disclosed. The plasma system includes: a plasma device including an electrode formed from a metal alloy and a dielectric layer covering the electrode, the dielectric layer including a distal portion extending distally past a distal end of the electrode by a predetermined distance; a liquid source configured to supply a liquid to a workpiece; an ionizable media source coupled to the plasma device and configured to supply ionizable media thereto; and a power source coupled to the electrode and configured to ignite the ionizable media at the plasma device to form a plasma effluent in the presence of the liquid, whereby the plasma effluent reacts with the liquid to form at least one reactive species that interacts with the workpiece.

A method for treatment of a workpiece is also disclosed. The method includes: supplying a liquid to a workpiece; positioning a plasma device adjacent to the workpiece; supplying ionizable media to the plasma device; and igniting the ionizable media at the plasma device sufficient to form a plasma effluent at a distal portion thereof in the presence of the liquid, whereby the plasma effluent reacts with the liquid to form at least one reactive species that interacts with the workpiece.

A method for treatment of a workpiece is contemplated by the present disclosure. The method includes: supplying a liquid to a workpiece; positioning a plasma device adjacent to the workpiece, wherein the plasma device includes an electrode formed from a metal alloy and including a dielectric layer slideably disposed over the electrode, the dielectric layer including a distal portion extending distally past a distal end of the electrode by an exposure distance; supplying ionizable media and at least one precursor feedstock to the plasma device; igniting the ionizable media and the at least one precursor feedstock at the plasma device sufficient to form a plasma effluent at the distal portion in the presence of the liquid, whereby the plasma effluent reacts with the liquid to form at least one reactive species that interacts with the workpiece; and adjusting at least one of a submersion distance of the plasma device and the exposure distance to regulate temperature of the plasma effluent.

BRIEF DESCRIPTION OF THE DRAWINGS

The accompanying drawings, which are incorporated in and constitute a part of this specification, illustrate exemplary embodiments of the disclosure and, together with a general description of the disclosure given above, and the detailed description of the embodiments given below, serve to explain the principles of the disclosure, wherein:

FIGS. 8A and 8B shows photographs illustrating lesions formed on bone tissue using plasma according to the present disclosure;

FIG. 9 shows a photograph illustrating a lesion formed on bone tissue using plasma according to the present disclosure;

DETAILED DESCRIPTION

Plasmas are generated using electrical energy that is delivered as either direct current (DC) electricity or alternating current (AC) electricity at frequencies from about 0.1 hertz (Hz) to about 100 gigahertz (GHz), including radio frequency ("RF", from about 0.1 MHz to about 100 MHz) and microwave ("MW", from about 0.1 GHz to about 100 GHz) bands, using appropriate generators, electrodes, and antennas. Choice of excitation frequency, the workpiece, as well as the electrical circuit that is used to deliver electrical energy to the circuit affects many properties and requirements of the plasma. The performance of the plasma chemical generation, the delivery system and the design of the electrical excitation circuitry are interrelated—as the choices of operating voltage, frequency and current levels (as well as phase) effect the electron temperature and electron density. Further, choices of electrical excitation and plasma device hardware also determine how a given plasma system responds dynamically to the introduction of new ingredients to the host plasma gas or liquid media. The corresponding dynamic adjustment of the electrical drive, such as via dynamic match networks or adjustments to voltage, current, or excitation frequency may be used to maintain controlled power transfer from the electrical circuit to the plasma.

Figure 1:
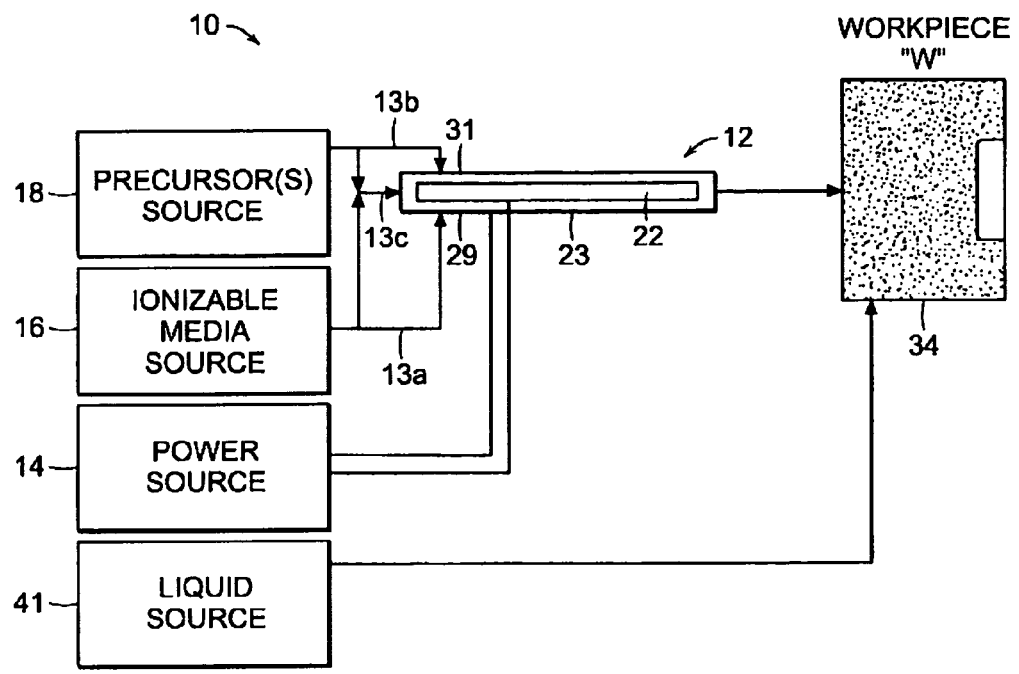
FIG. 1 is a schematic diagram of a plasma system according to the present disclosure.

Referring initially to FIG. 1, a plasma system 10 is disclosed. The system 10 includes a plasma device 12 that is coupled to a power source 14, an ionizable media source 16 and a precursor source 18. Power source 14 includes any suitable components for delivering power or matching impedance to plasma device 12. More particularly, the power source 14 may be any radio frequency generator or other suitable power source capable of producing power to ignite the ionizable media to generate plasma. The plasma device 12 may be utilized as an electrosurgical pencil for application of plasma to tissue and the power source 14 may be an electrosurgical generator that is adapted to supply the device 12 with electrical power at a frequency from about 0.1 MHz to about 2,450 MHz, in embodiments, from about 1 MHz to about 160 MHz. In another embodiment, electrical power may be supplied at two or more different frequencies (e.g., 13.56 MHz and 60 MHz). The plasma may also be ignited by using continuous or pulsed direct current (DC) electrical energy as well as continuous or pulsed RF energy or combinations thereof.

The precursor source 18 may be a bubbler or a nebulizer configured to aerosolize precursor feedstocks prior to introduction thereof into the device 12. The precursor source 18 may also be a micro droplet or injector system capable of generating predetermined refined droplet volume of the precursor feedstock from about 1 femtoliter to about 1 milliliter in volume. The precursor source 18 may also include a microfluidic device, a piezoelectric pump, or an ultrasonic vaporizer.

The system 10 provides a flow of plasma through the device 12 to a workpiece "W" (e.g., tissue). The workpiece "W" may be any type of material or object suitable for plasma treatment. Plasma feedstocks, which include ionizable media and precursor feedstocks, are supplied by the ionizable media source 16 and the precursor source 18, respectively, to the plasma device 12. During operation, the precursor feedstock and the ionizable media are provided to the plasma device 12 where the plasma feedstocks are ignited to form plasma effluent containing ions, radicals, photons from the specific excited species and metastables that carry internal energy to drive desired chemical reactions in the workpiece "W" or at the surface thereof. The feedstocks may be mixed upstream from the ignition point or midstream thereof (e.g., at the ignition point) of the plasma effluent, as shown in FIG. 1 and described in more detail below.

The ionizable media source 16 provides ionizable feedstock to the plasma device 12. The ionizable media source 16 is coupled to the plasma device 12 and may include a storage tank and a pump (not explicitly shown). The ionizable media may be a liquid or a gas such as argon, helium, neon, krypton, xenon, radon, carbon dioxide, nitrogen, hydrogen, oxygen, etc. and their mixtures, and the like, or a liquid. These and other gases may be initially in a liquid form that is gasified during application.

The precursor source 18 provides precursor feedstock to the plasma device 12. The precursor feedstock may be either in solid, gaseous or liquid form and may be mixed with the ionizable media in any state, such as solid, liquid (e.g., particulates or droplets), gas, and the combination thereof. The precursor source 18 may include a heater, such that if the precursor feedstock is liquid, it may be heated into gaseous state prior to mixing with the ionizable media.

In one embodiment, the precursors may be any chemical species capable of forming reactive species following plasma drive dissociation, such as ions, electrons, excited-state (e.g., metastable) species, molecular fragments (e.g., radicals) and the like, when ignited by electrical energy from the power source 14 or when undergoing collisions with particles (electrons, photons, or other energy-bearing species of limited and selective chemical reactivity) formed from ionizable media 16. More specifically, the precursors may include various reactive functional groups, such as acyl halide, alcohol, aldehyde, alkane, alkene, amide, amine, butyl, carboxlic, cyanate, isocyanate, ester, ether, ethyl, halide, haloalkane, hydroxyl, ketone, methyl, nitrate, nitro, nitrile, nitrite, nitroso, peroxide, hydroperoxide, oxygen, hydrogen, nitrogen, and combination thereof. In embodiments, the chemical precursors may be water, halogenoalkanes, such as dichloromethane, tricholoromethane, carbon tetrachloride, difluoromethane, trifluoromethane, carbon tetrafluoride, and the like; peroxides, such as hydrogen peroxide, acetone peroxide, benzoyl peroxide, and the like; alcohols, such as methanol, ethanol, isopropanol, ethylene glycol, propylene glycol, alkalines such as NaOH, KOH, amines, alkyls, alkenes, and the like. Such chemical precursors may be applied in substantially pure, mixed, or soluble form.

The precursors and their functional groups may be delivered to a surface to react with the surface species (e.g., molecules) of the workpiece "W." In other words, the functional groups may be used to modify or replace existing surface terminations of the workpiece "W." The functional groups react readily with the surface species due to their high reactivity and the reactivity imparted thereto by the plasma. In addition, the functional groups are also reacted within the plasma volume prior to delivering the plasma volume to the workpiece.

Some functional groups generated in the plasma can be reacted in situ to synthesize materials that subsequently form a deposition upon the surface. This deposition may be used for stimulating healing, killing bacteria, and increasing hydrophilic or hydroscopic properties. In addition, deposition of certain function groups may also allow for encapsulation of the surface to achieve predetermined gas/liquid diffusion, e.g., allowing gas permeation but preventing liquid exchange, to bond or stimulate bonding of surfaces, or as a physically protective layer.

The precursor source 18 and the ionizable media source 16 may be coupled to the plasma device 12 via tubing 13a and 13b, respectively. The tubing 13a and 13b may be combined into tubing 13c to deliver a mixture of the ionizable media and the precursor feedstock to the device 12 at a proximal end thereof. This allows for the plasma feedstocks, e.g., the precursor feedstock and the ionizable gas, to be delivered to the plasma device 12 simultaneously prior to ignition of the mixture therein.

In another embodiment, the ionizable media source 16 and the precursors source 18 may be coupled to the plasma device 12 via the tubing 13a and 13b at separate connections, e.g., the first connection 31 and a second connection 29, respectively, such that the mixing of the feedstocks occurs within the plasma device 12 upstream from the ignition point. In other words, the plasma feedstocks are mixed proximally of the ignition point, which may be any point between the respective sources 16 and 18 and the plasma device 12, prior to ignition of the plasma feedstocks to create the desired mix of the plasma effluent species for each specific surface treatment on the workpiece "W."

In a further embodiment, the plasma feedstocks may be mixed midstream, e.g., at the ignition point or downstream of the plasma effluent, directly into the plasma. More specifically, the first and second connections 31, 29 may be coupled to the device 12 at the ignition point, such that the precursor feedstocks and the ionizable media are ignited concurrently as they are mixed (FIG. 1). It is also envisioned that the ionizable media may be supplied to the device 12 proximally of the ignition point, while the precursor feedstocks are mixed therewith at the ignition point.

In a further illustrative embodiment, the ionizable media may be ignited in an unmixed state and the precursors may be mixed directly into the ignited plasma. Prior to mixing, the plasma feedstocks may be ignited individually. The plasma feedstock is supplied at a predetermined pressure to create a flow of the medium through the device 12, which aids in the reaction of the plasma feedstocks and produces a plasma effluent. The plasma according to the present disclosure is generated at or near atmospheric pressure under normal atmospheric conditions.

The system 10 also includes a liquid source 40 that may include a pump or may be a gravity-fed system. The liquid source 40 is configured to supply a liquid media 34 (FIG. 4) to the workpiece "W" by submerging or otherwise irrigating the workpiece "W."

Figure 2:
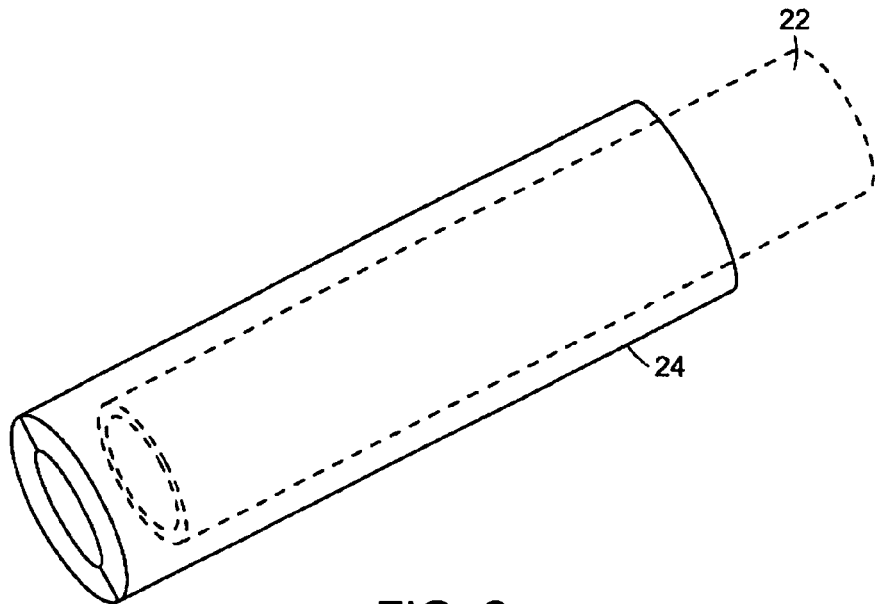
FIG. 2 is a perspective, cross-sectional view of a plasma device according to the present disclosure.

With reference to FIGS. 1-4, the device 12 includes an electrode 22. As shown in FIG. 2, the electrode 22 has a substantially cylindrical tubular shape having lumen 29 (FIG. 3) defined therein. The electrode 22 may be formed from a conductive material suitable for ignition of plasma such as metals and metal-ceramic composites. In one embodiment, the electrode 22 may be formed from a conductive metal including a native oxide or nitride compound disposed thereon.

The electrode 22 is coupled to the power source 14 that drives plasma generation, such that the energy from the power source 14 may be used to ignite the plasma feedstocks flowing through the device 12. More specifically, the ionizable media and the precursors flow through the device 12 through the lumen 29. When the electrode 22 is energized, the plasma feedstocks are ignited and form a plasma effluent which is emitted from the distal end of the device 12 onto the workpiece "W."

In one embodiment, the device 12 may include an optional return electrode. The return electrode may be shaped as a ring and may be disposed distally of the electrode 22. In another embodiment, the electrode 22 may be used without a return electrode since coupling is provided through the workpiece "W."

Figure 3:
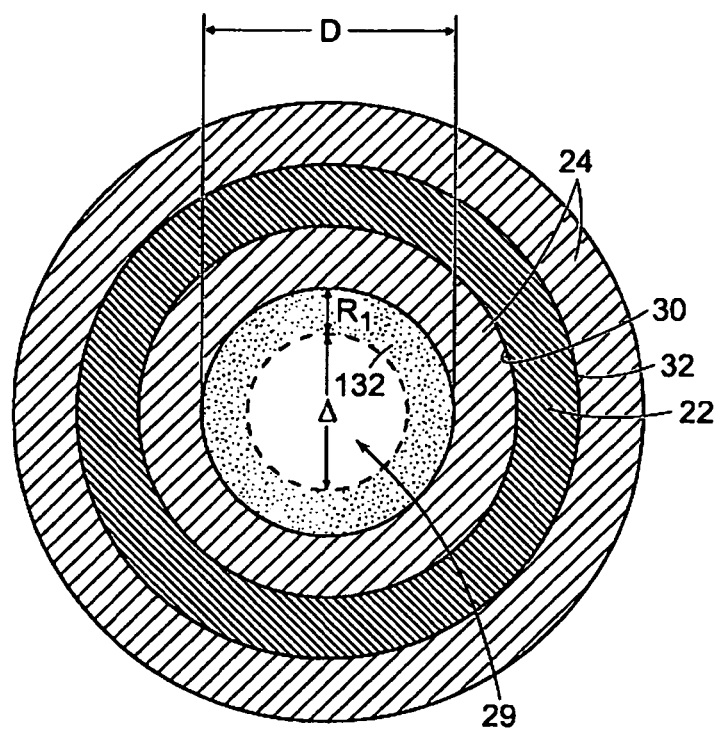
FIG. 3 is a side, cross-sectional view of the plasma device of FIG. 2 according to the present disclosure.
Figure 4:
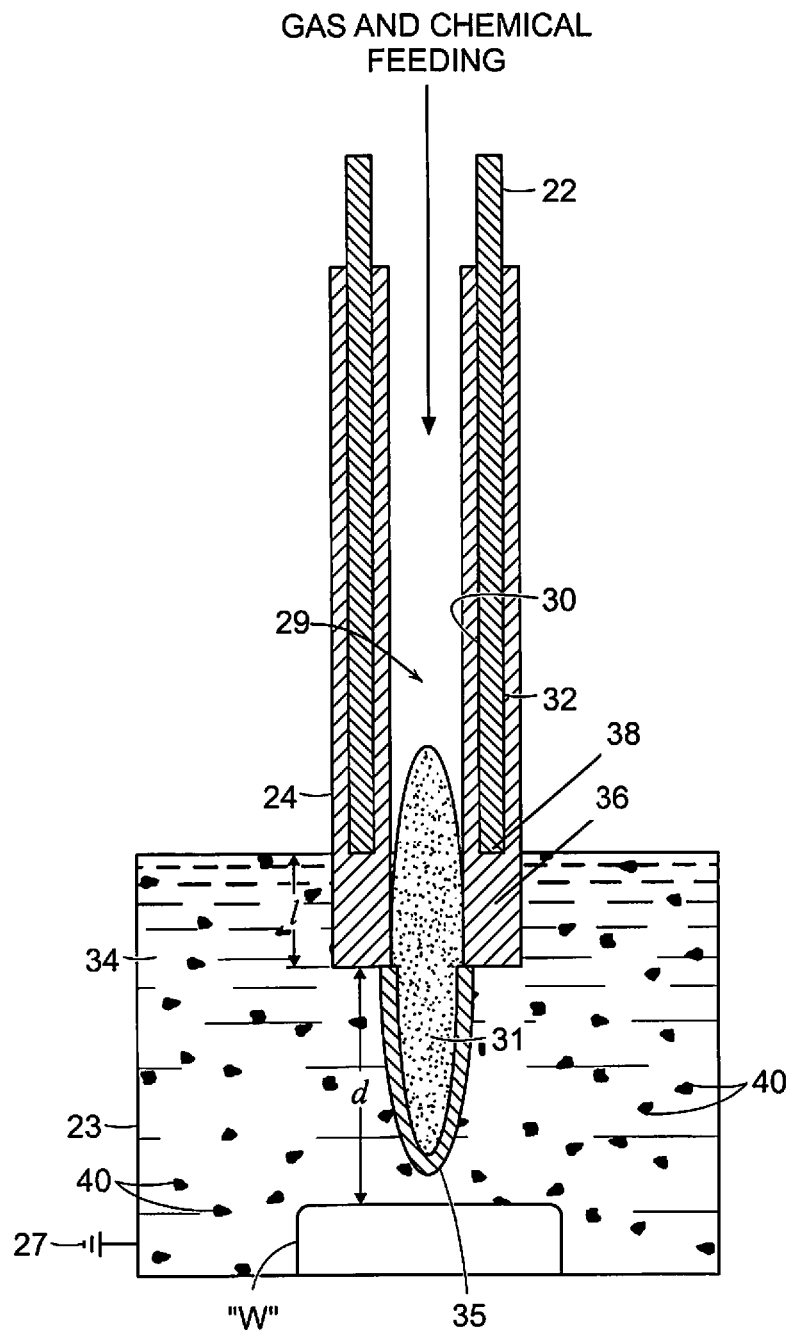
FIG. 4 is a front, cross-sectional view of the plasma device of FIG. 2 according to the present disclosure.

As shown in FIGS. 2-4, the electrode 22 includes a dielectric layer 24 that covers inner and outer surfaces 30, 32 of the electrode 22. The layer 24 may be formed from an insulative or semiconductive material deposited as a film onto the inner conductor (e.g., atomic layer deposition) or as a dielectric sleeve or layer. In one illustrative embodiment, the insulative layer 24 may be a native metal oxide. The layer 24 limits the plasma action to the distal portion of the electrode 22 and provides for the creation of a plasma effluent 31 having high energy electrons.

In addition, the layer 24 provides for capacitive coupling between the electrode 22 and the ionizable media and/or precursor feedstock. The resulting capacitive circuit element structure provides for a net negative bias potential at the surface of the electrode 22, which attracts the ions and other species from the plasma effluent. These species then bombard the layer 24 and release the electrons generating additional high energy electrons.

The layer 24 may be a native oxide, or a native nitride of the metal from which the electrode 22 is formed, or may be a deposited layer or a layer formed by ion implantation. In one illustrative embodiment, the electrode 22 is formed from an aluminum alloy and the layer 24 is aluminum oxide ($Al_2O_3$) or aluminum nitride (AlN). In another illustrative embodiment, the electrode 22 is formed from a titanium alloy and the layer 24 is titanium oxide ($TiO_2$) or titanium nitride (TiN).

The electrode 22 and the layer 24 may also be configured as a heterogeneous system. The electrode 22 may be formed from any suitable electrode substrate material (e.g., conductive metal or a semi-conductor) and the layer 24 may be disposed thereon by various coating processes. The layer 24 may be formed on the electrode 22 by exposure to an oxidizing environment, anodization, electrochemical processing, ion implantation, or deposition (e.g., sputtering, chemical vapor deposition, atomic layer deposition, etc.).

In embodiments, the layer 24 may also be formed from suitable dielectric polymeric materials, such as polytetrafluoroethylene, polypropylene, polyethylene, fluoroethylpropylene, and combinations thereof.

The high energy electrons are generated in part by the materials of the electrode 22 and in particular by the layer 24. Materials having high secondary electron emission property, γ, in response to ion and/or photon bombardment are suitable for this task. Such materials include insulators and/or semiconductors. These materials have a relatively high γ, where γ represents the number of electrons emitted per incident bombardment particle. Thus, metals generally have a low γ (e.g., less than 0.1) while insulative and semiconductor materials, such as metallic oxides have a high γ, from about 1 to about 10 with some insulators exceeding a value of 20. Thus, the layer 24 acts as a source of secondary emitted electrons, in addition to limiting the plasma to the distal end of the electrode 22.

Secondary electron emission, γ, may be described by the formula (1):

$$\gamma \leq \Gamma_{secondary}/\Gamma_{ion} \qquad (1)$$

In formula (1) γ is the secondary electron emission yield or coefficient, $\Gamma_{secondary}$ is the electron flux, and $\Gamma_{ion}$ is the ion flux. Secondary emission occurs due to the impacts of plasma species (ions) onto the layer 24 when the ion impact collisions have sufficient energy to induce secondary electron emission, thus generating γ-mode discharges. Generally discharges are said to be in γ-mode when electron generation occurs preferentially at electrode surfaces (i.e., γ>1) instead of in the gas (an α-mode discharge). In other words, per each ion colliding with the layer 24, a predetermined number of secondary electrons are emitted. Thus, γ may also be thought of as a ratio of the $\Gamma_{secondary}$ (e.g., the electron flux) and $\Gamma_{ion}$ (e.g., the ion flux).

These ion collisions with the surface of the layer 24, in turn, provide sufficient energy for secondary electron emission to generate γ discharges. The ability of coating materials such as layer 24 to generate γ discharges varies with several parameters, with the most influence due to the choice of materials having a high γ as discussed above. This property allows coatings 24 to act as a source of secondary emitted electrons or as a catalytic material to enhance selected chemical reaction paths.

Over time the layer 24 may thin or be removed during the plasma operation. In order to maintain the layer 24 to continually provide a source of secondary emitted electrons, the layer 24 may be continually replenished during the plasma operation. This may be accomplished by adding species that reformulate the layer 24 on the electrode 22. In one embodiment, the precursor source 18 may provide either oxygen or nitrogen gas to the device 12 to replenish the oxide or nitride coating.

Secondary electron emission forms a sheath layer 132 about the electrode 22. The sheath layer has a working range $R_1$, which is representative of the thickness of energetic electron sheath layer 132 disposed about the inner circumference of electrode 22. In other words, the range $R_1$ indicates a region with a greatly increased concentration of electrons with relatively high energies that drive reactions in the gas phase. The coating on the electrode 22 can increase or enhance working range $R_1$ of energetic secondary electrons. In particular, varying the thickness of the coating can be used to adjust the working range $R_1$. A gap distance A shows the zone where the concentration of energetic secondary electrons is relatively lower. Coating the electrodes, as discussed above, reduces gap distance Δ. In some embodiments, distance A may be reduced to zero and/or working range $R_1$ may overlap thereby creating a hollow cathode effect. Namely, the range $R_1$ is large enough to fully envelop the inner diameter D of the lumen 29.

Formation of the sheath layer 132 may also be controlled by the supply of the ionizable media and the precursors. Ionizable media and the precursors are selected that are relatively transparent to the energetic electrons released during secondary emission from the surface of the coating. As stated above, the plasma is generated at atmospheric pressure. Due to the increased entropy at such pressure, the generated electrons undergo a multitude of collisions in a relatively short period of time and space forming the sheath layer 132.

Generation of the high energy electrons is also controlled by the supply of the ionizable media and the precursors. Ionizable media and the precursors are selected that are relatively transparent to the energetic electrons released during secondary emission from the surface of the electrode 22. As stated above, the plasma is generated at atmospheric pressure. Due to the increased entropy at such pressure, the generated electrons undergo a multitude of collisions in a relatively short period of time and space forming the high energy electrons.

The reaching distance of the high energy electrons is defined by a formula (2):

$$\text{Thickness} = 1/N\sigma \quad (2)$$

In formula (2), N is the number of scattering centers, which may be the molecules of the ionizable media, the precursors and the atmospheric gases. Thus, N defines the media density. The variable, σ, is the average particle cross-section of the scattering centers. The thickness of the high energy electrons is inversely proportional to the product of N and σ. Thus, decreasing N and σ allows for generating more high energy electrons. A lower σ may be provided by using specific ionizable media compounds with molecules having a low cross-section, such as hydrogen and helium. The variable N may be lowered by heating the ionizable media to reduce the gas density and limiting the amount of media provided to the lowest amount needed to sustain the plasma reaction.

With respect to FIG. 4, the present disclosure provides for a system and method of generating the plasma effluent 31 in a liquid media 34. The workpiece "W" is also submerged in the liquid media 34 allowing the plasma effluent 31 to perform treatment thereof. The plasma effluent 31 is formed within the lumen 29 and is restricted by the dielectric layer 24. In particular, the dielectric layer 24 includes a distal portion 36 that extends distally past a distal end 38 of the electrode 22 by a predetermined distance "l."

The liquid media 34 may be saline, deionized water or an aqueous solution of various salts (e.g., NaCl) and/or other chemical precursors from about $1 \times 10^{-4}$ M to about $1 \times 10^{-2}$ M. In embodiments, dilute acids may also be added to the liquid media 34, including HCl, $H_2SO_4$ and the like having pH from about 3 to about 5. In embodiments, bases such as, NaOH, KOH, may also be added. Various reactive gases such as chloride, flouride, ozone, bromine, and the like may also be added to the liquid media 34.

In embodiments, catalysts 40 may be added to the liquid media 34 as shown in FIG. 4. In another embodiment, catalysts 40 may be embedded in the dielectric layer 24. Catalysts 40 may be added in amounts from about 1% to about 50% by volume, in embodiments from about 10% to about 40% by volume. Exemplary catalysts 40 include metal oxides such as $TiO_2$ or any other suitable catalysts 40 that generate hydroxide radicals when mixed with water. The catalysts 40 may be in the form of nanoparticles having a volume average diameter from about 0.1 nm to about 1,000 nm, in embodiments from about 5 nm to about 500 nm. Addition of catalysts 40 reduces interface temperature between the plasma effluent 32 and the liquid media 34 since catalysts 40 aid in the generation of reactive radicals at low power.

In one embodiment, DC bias may be supplied to the electrode 22 in addition to the RF power. This allows for control over the mobility of the charged particles into the plasma effluent 31. In particular, the DC bias accelerates the charged particles allowing them to reach the workpiece "W." The charge particles accumulate at the plasma/liquid interface 35 and modify the chemical reactions at the plasma/liquid interface 35 from an equilibrium or bulk state to a non-equilibrium state. The non-equilibrium state gives rise to a selective chemical reaction at the plasma/liquid interface 35, which aids in controlling specific chemical reactions and selective removal processes.

During use, the plasma device 12 may be submerged in the liquid media 34 up to a desired depth, such that the distal portion 36 is disposed a predetermined submerged distance "d" from the workpiece "W." The submerged distance "d" may be adjusted by simply moving the device 12 in and out of the liquid media 34. In another embodiment, the dielectric layer 34 may be slideably disposed over the electrode 22 allowing for adjustment of the distance "l" by moving the dielectric layer 34 along the electrode 22.

This configuration prevents the generation of arcing and plays an important role in controlling the chemical reaction between the plasma effluent 31 and the liquid media 34 at the plasma/liquid interface 35. Submerging of the distal portion 36 concentrates the plasma effluent 31 into discharging within the liquid media 34. The submerged distance "d" is directly proportional to the temperature of the plasma effluent 31. Thus, the deeper the electrode 22 is submerged, the hotter the plasma effluent 31 becomes. Conversely, withdrawing the electrode 22 from the liquid media 34 decreases the temperature of the plasma effluent 31. This is due to the heat removal properties of the liquid media 34, since the distance "d" directly relates to the exposure of the plasma effluent 31 to the liquid media 34, which acts as a heatsink. This relationship between the submerging distance "d" and the temperature may be used to generate particular surgical effects at the workpiece "W." In particular, varying the temperature of the plasma effluent 31 directly effects the hemostasis effect thereof.

The liquid media 34 and the workpiece "W" may be placed within a container 23. The container 23 may be formed from a conductive material and may be coupled to a ground terminal 27 of the generator 14. In another embodiment, the ground terminal 27 may be an electrode that is placed in the vicinity of the electrode 22 within the liquid media 34.

As discussed above, the ionizable media and the precursor feedstocks are supplied through the lumen 29 and energy is supplied to the electrode 22 to ignite the mixture to form the plasma effluent 31. The ionizable media may be selected to include components (e.g., Ar, He, etc.) that assist plasma action and/or improve plasma chemical processes of breaking down feedstocks into reactive species. The plasma effluent 31 is ignited and sustained by electrical energy that is delivered through the electrode 22.

The plasma effluent 31 is injected into the liquid media 34, thereby generating additional chemical reactions between the volatized components of the ionized media and feedstocks and constituents of the liquid media 34 (e.g., water molecules, ions, etc.). This results in further dissociation (e.g., breaking down of molecular components into constituents) of feedstocks, media, etc. and dispersion thereof into the liquid media 34. More specifically, interaction between the plasma effluent 31 and the liquid media 34 allows for local in-situ generation of radicals and metastable atoms and/or molecules that react with the surface of the workpiece "W." In addition to chemical reactions, the physical force due to the flow of the plasma effluent 31 also acts on (e.g, etches) the workpiece "W" with increased chemical reaction rates.

Figure 5:
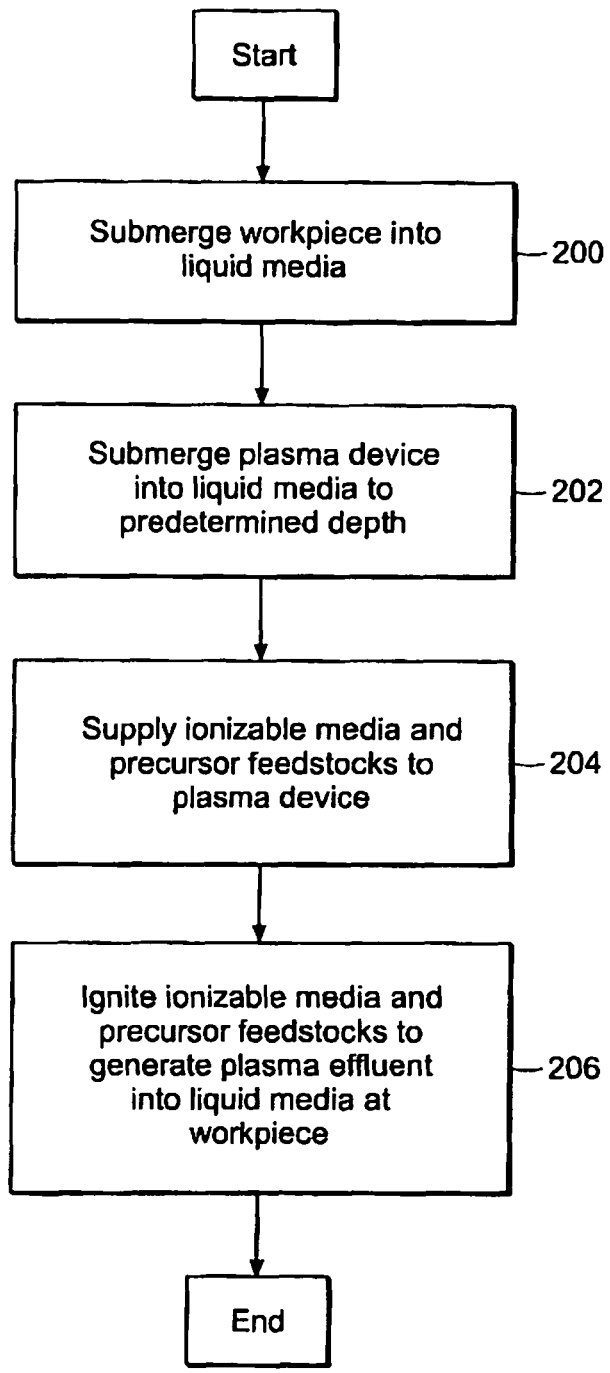
FIG. 5 is a flow chart diagram of a method of plasma tissue treatment according to the present disclosure.

FIG. 5 illustrates a method of applying the plasma effluent 31 to the workpiece "W" submerged in the liquid media 34. In step 200, the liquid media 34 is supplied locally to the workpiece "W" via irrigation and other suitable techniques to submerge the workpiece "W" in the liquid media 34. In step 202, the plasma device 12 is also submerged into the liquid media 34. The submerged depth "d" and the exposure distance "l" may be adjusted to achieve a desired temperature of the plasma effluent 31 as discussed above. The layer 24 may include a marking on the outside surface thereof to indicate the maximum submersion depth of the electrode 22. In step 204, the ionizable media and precursor feedstocks are supplied to the plasma device 12 and are ignited in step 206 therein to form the plasma effluent 31 within the liquid media 34. The plasma effluent 31 interacts with the liquid media 34 to form chemically reactive species that bombard the surface of the workpiece "W." The plasma device 12 may be maintained at the workpiece "W" for any period of time until the desired tissue effect is achieved. Certain tissue effects may be achieved in relatively short period of time (e.g., bone etching) whereas other procedures (e.g., destruction of the bone tissue) may require dwell times from about 1 minute to about 2 minutes.

The plasma device 12 may also be utilized for whitening teeth. In this embodiment, the liquid media 34 may be deionized water, carbamide peroxide, an aqueous basic solution with sodium hydroxide and other suitable bases, as well as other suitable hydroxide ($OH^-$) and hydrogen ($H^+$) radical donors. The teeth may be submerged in the liquid media 34 (e.g., via irrigation and circulation of the deionized water through the mouth). The plasma device 12, namely, the electrode 22 is submerged into the liquid media 34 to a desired depth. The plasma device 12 may be provided with suitable chemical precursors suitable for removing foreign matter (e.g., stains, plaque, etc.) disposed on tooth enamel, such as oxygen, nitrogen dioxide, carbon dioxide and mixtures thereof. In another embodiment, the plasma device 12 may be used without chemical precursor feedstocks since deionized water provides suitable chemical feedstocks for the whitening procedure.

In a further embodiment, the liquid media 34 may also include a precursor feedstock dissolved therein. The supplied precursors feedstocks or feedstocks dissolved in the liquid media 34 may be chosen for their selectivity in reacting with the foreign matter (e.g., stains, plaque, etc.) disposed on tooth enamel. In other words, the selected precursor feedstocks have higher chemical reactivity with the foreign matter relative to the chemical reactivity with the enamel tissue. Without being limited to any particular theory, it is believed that one specific reaction illustrated by formula (3) may be responsible for the bleaching action:

$$H_2O+e^- \rightarrow OH^- + H^+ + e^- \qquad (3)$$

The reaction depicted by formula (3) occurs at the plasma/liquid interface 35 and is characterized by the formation of hydroxide ($OH^-$) and hydrogen ($H^+$) radicals due to the energy supplied to the water molecules by the plasma effluent 31. In addition, other radicals may also be formed at the plasma/liquid interface 35, such as oxides and hydrides. The generated radicals bombard the build-up of foreign matter on the teeth thereby whitening the teeth. More specifically, the radicals and other plasma-generated species break the bonds of the build-up into constituent compounds, which are then dissolved in the liquid media 34.

Figure 6:
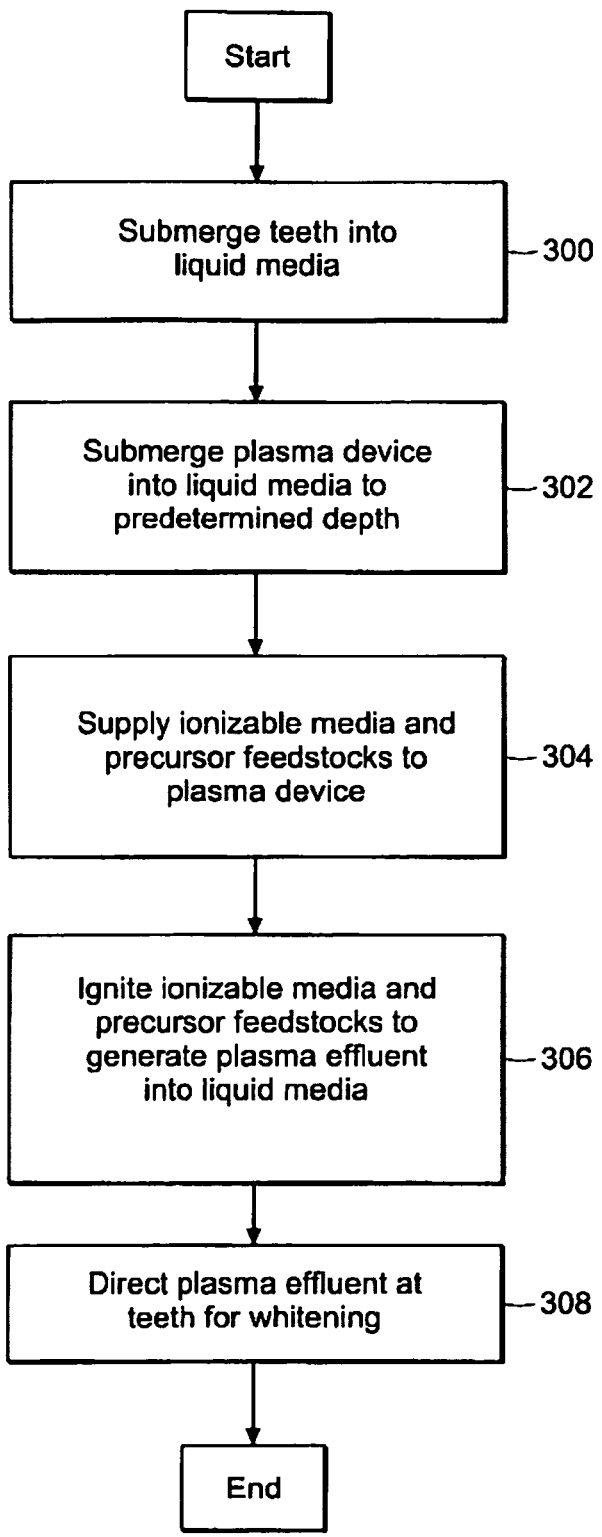
FIG. 6 is a flow chart diagram of another method of plasma tissue treatment according to the present disclosure.

FIG. 6 illustrates a method of applying the plasma effluent 31 to whiten teeth. In step 300, the liquid media 34, namely, deionized water, is supplied locally to the teeth via irrigation and other suitable techniques to surround the teeth in the liquid media 34. The liquid media 34 is supplied in a sufficient amount to at least partially submerge a portion of a tooth. In step 302, the plasma device 12 is also submerged into the liquid media 34. The submerged depth "d" and the exposure distance "l" may be adjusted to achieve a desired temperature of the plasma effluent 31 as discussed above. The distal portion 34 may be placed directly in contact with the teeth. In step 304, the ionizable media is supplied to the plasma device 12 and is ignited in step 306 therein to form the plasma effluent 31 within the liquid media 34. The plasma effluent 31 interacts with the liquid media 34 to form hydroxide, hydrogen, hydride and oxide radicals as well as other plasma-generated species that bombard the surface of the teeth. The plasma device 12 may be maintained at the teeth for any period of time until the desired whitening effect is achieved. Certain tissue effects may be achieved in relatively short period of time (e.g., plaque removal) whereas other procedures (e.g., stain removal) may require longer dwell times.

In one embodiment, the plasma device 12 may be used to apply hydrophobic compounds such as hexamethyldisiloxane ("HMDSO") and $CF_4$ to the workpiece "W" to generate a hydrophobic coating on the surface thereof. The hydrophobic compounds may be supplied to the plasma through the precursor source 18. The hydrophobic compounds are mixed with the ionizable media and are volatized within the plasma device 12 and are then deposited on the workpiece "W" by the plasma effluent 31. Hydrophobic plasma-applied coating may be suitable for preventing bacterial growth on living tissue. In embodiments, the hydrophobic coating may be applied to the teeth to minimized growth of bacteria once the foreign matter has been removed from enamel of teeth.

Figure 7:
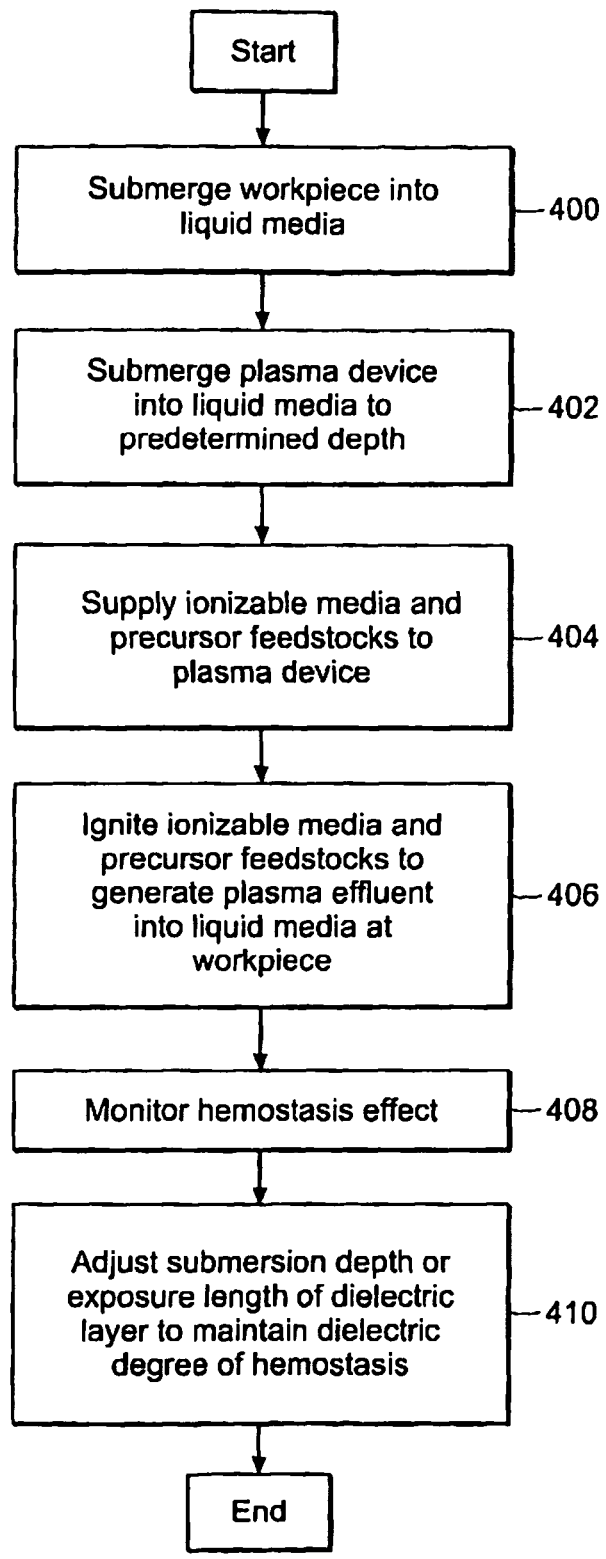
FIG. 7 is a flow chart diagram of a further method of plasma tissue treatment according to the present disclosure.

FIG. 7 illustrates a method of applying the plasma effluent 31 to cartilage tissue in an abrasion arthroplasty procedure. In step 400, the liquid media 34 is supplied locally to the workpiece "W" (e.g., cartilage) via irrigation and other suitable techniques to submerge the workpiece "W" in the liquid media 34. In step 402, the plasma device 12 is also submerged into the liquid media 34. The submerged distance "d" and the exposure distance "l" may be adjusted to achieve a desired temperature of the plasma effluent 31 as discussed above. In step 404, the ionizable media and precursor feedstocks are supplied to the plasma device 12 and are ignited in step 406 therein to form the plasma effluent 31 within the liquid media 34. The plasma effluent 31 interacts with the liquid media 34 to form chemically reactive species that bombard the surface of the workpiece "W." The plasma device 12 may be maintained at the workpiece "W" for any period of time until the desired tissue effect is achieved. Certain tissue effects may be achieved in relatively short period of time (e.g., bone etching) whereas other procedures (e.g., destruction of the bone tissue) may require dwell times from about 1 minute to about 2 minutes. In step 408, the hemostasis effect of the plasma effluent 31 is monitored. Since the goal of the abrasion arthroplasty procedure is to generate as many stem cells as possible via bleeding, hemostasis must be minimized. In step 410, the submersion depth "d" is adjusted to maintain a desired degree of hemostasis or lack thereof.

EXAMPLE 1

Bone Etching

FIGS. 8A and 8B illustrate the effect of the above-discussed plasma effluent on bone tissue supplied thereto in a liquid environment. In each example, bone tissue was submerged in deionized water and NaCl was added to the water to provide chloride ions (e.g., from NaCl) as a chemical precursor for forming localized lesions. The electrode was submerged into the liquid and plasma generation was initiated and maintained for two (2) minutes. The lesion in FIG. 7A was formed using an electrode having a distal portion that is submerged to the submersion distance "d" of larger than 2 mm, whereas FIG. 7B shows the effects formed by an electrode having a distal portion submerged to the submersion distance "d" of less than 2 mm. The effects of using smaller "d" are more pronounced as illustrated in FIG. 7B, which shows charring and other tissue removal due to the hotter temperature developed at the plasma effluent. The plasma effluent produced by the device at a shallow depth results in less charring but still removes the bone tissue. Lack of charring is due to a shallow submersion depth, which lowers the heat of the plasma effluent and its hemostasis effect.

FIG. 9 shows another photo illustrating the effects of application of the plasma effluent on bone tissue. Bone tissue was submerged in deionized water and NaCl was added to the water to provide chloride ions (e.g., from NaCl) as a chemical precursor for forming localized lesions. The electrode was submerged into the liquid and plasma generation was initiated and maintained for two (2) minutes. An electrode having a distal portion submerged to the submersion distance "d" of more than 2 mm was used to form the lesion. The plasma removed the bone tissue to the marrow region, which was also removed.

EXAMPLE 2

Tooth Whitening

Figure 10:
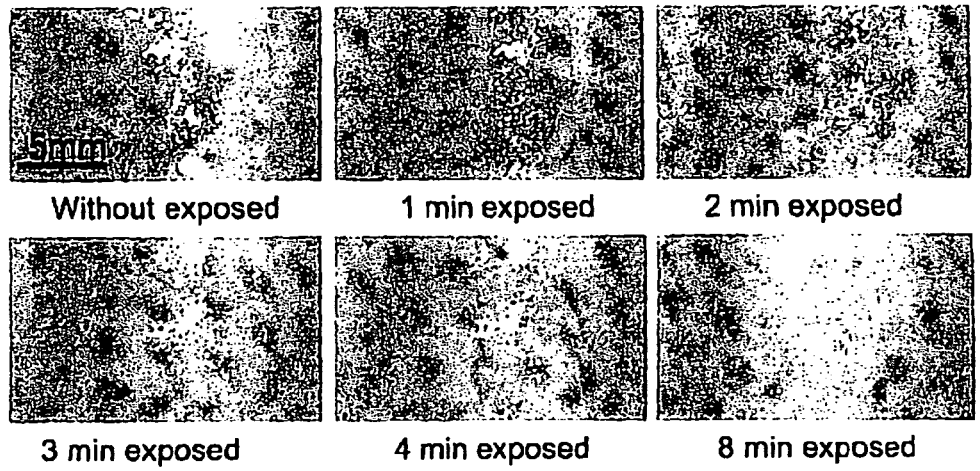
FIG. 10 shows a series of photographs illustrating effects of plasma on tooth whitening according to the present disclosure.

FIG. 10 illustrates the effectiveness of the above-discussed plasma on tooth whitening. FIG. 10 shows six photographs of a tooth taken prior to treatment and at various points in the treatment process, namely, at one, two, three, four and eight minutes. The tooth was submerged in deionized water and the electrode was brought in proximity with the tooth (e.g., submerged into the liquid). Argon gas was supplied to the plasma device and plasma generation was initiated and maintained for eight minutes. The photos illustrate the gradual progression of the treatment process and complete removal of the stain from the tooth.

Figures 11A, 11B:
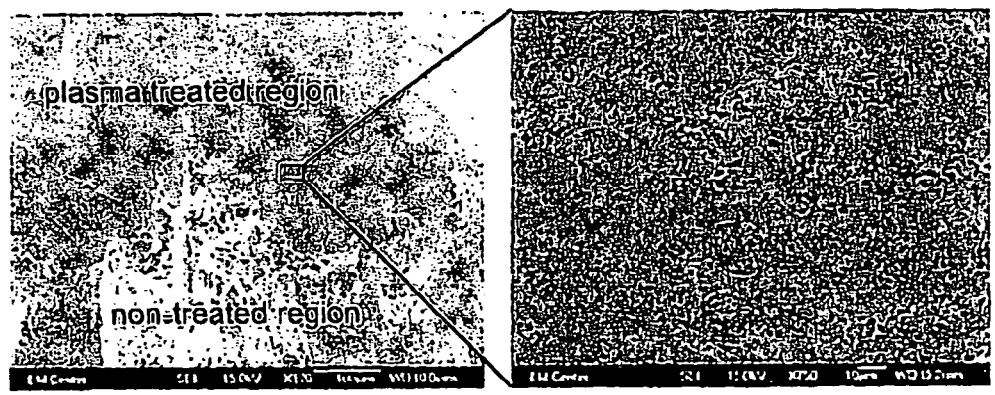
FIGS. 11A and 11B show scanning electron microscope images of a tooth whitened using plasma according to the present disclosure.

FIGS. 11A and 11B illustrate enlarged photos of the tooth. FIG. 11A shows the tooth at ×170 magnification illustrating the plasma treated region and a non-treated region and FIG. 11B shows the tooth at ×750 magnification in the treated region. The plasma-treated region shows a relatively smooth surface when compared with the non-treated region. The smooth surface is indicative of undamaged tooth enamel surface structure.

Figure 12:
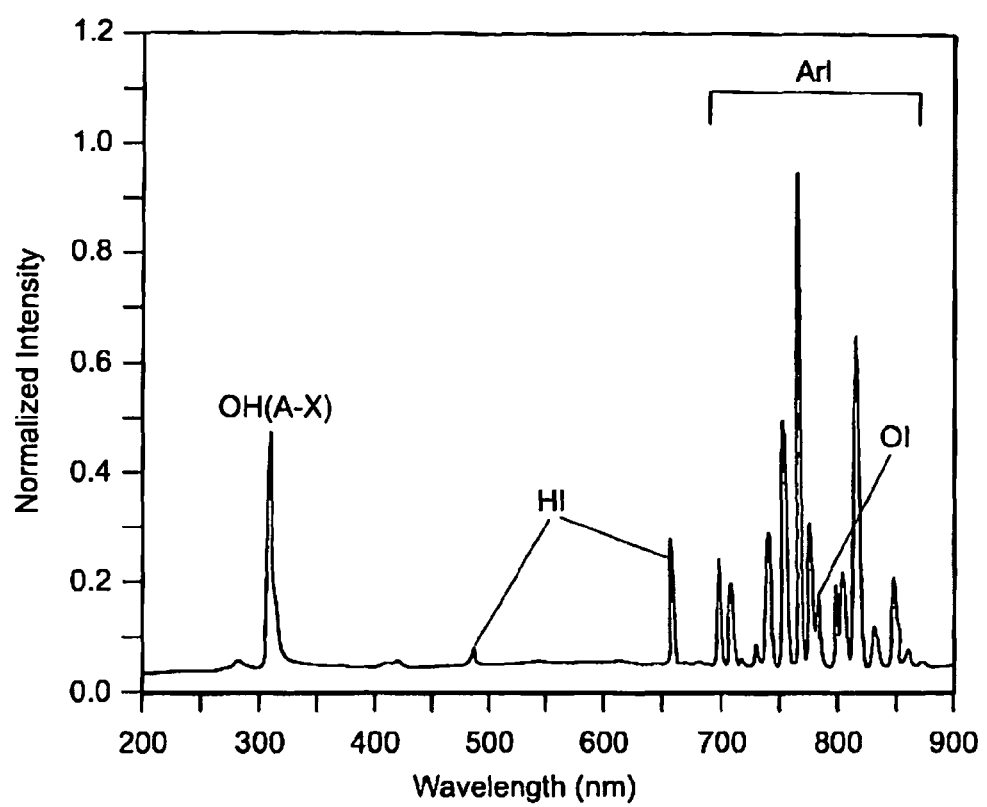
FIG. 12 shows an emission spectra of radicals generated by plasma according to the present disclosure.

FIG. 12 illustrates emission spectra of the plasma species produced by the plasma. The labeled peaks show the primary species identified in the plasma, as the hydroxide, hydrogen, oxygen and argon species. This supports the above-discussed explanation for the formula (3) being the primary vehicle of radical generation.

EXAMPLE 3

Catalysts in Liquid Media

Figure 13:
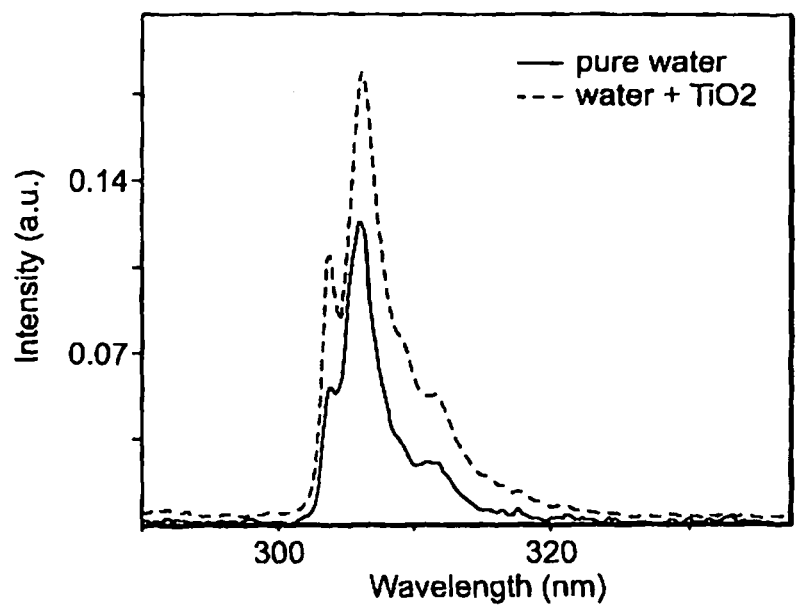
FIG. 13 shows an emission spectra of hydroxyl radicals generated by plasma in deionized water in the presence and in the absence of catalysts according to the present disclosure.
Figure 14:
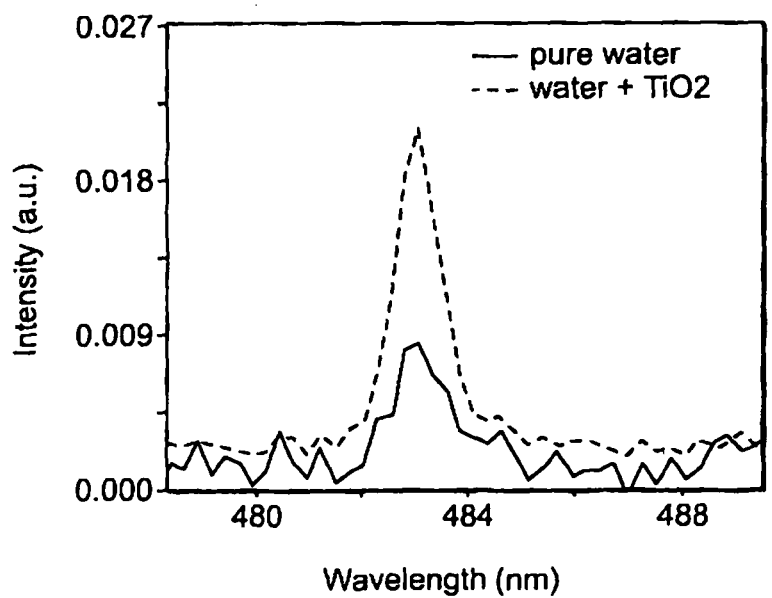
FIG. 14 shows an emission spectra of hydrogen alpha radicals generated by plasma in deionized water in the presence and in the absence of catalysts according to the present disclosure.
Figure 15:
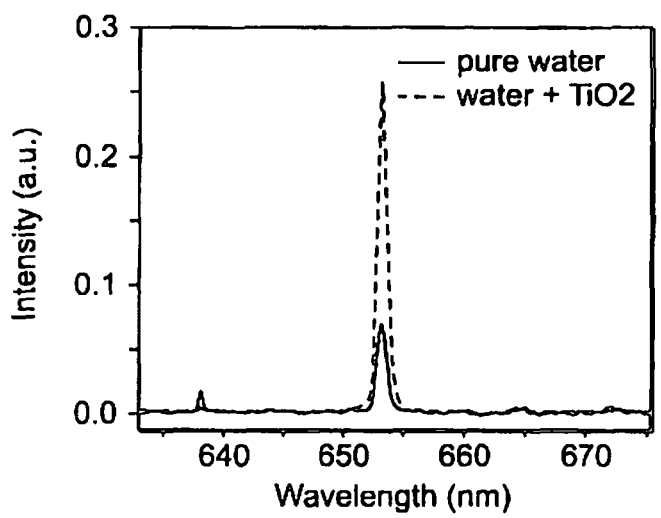
FIG. 15 shows an emission spectra of hydrogen beta radicals generated by plasma in deionized water in the presence and in the absence of catalysts according to the present disclosure.

Titanium oxide ($TiO_2$) catalysts were added into deionized water and plasma was generated within the water medium. The effectiveness of $TiO_2$ catalysts was measured by spectroscopy of hydroxyl (OH) and hydrogen (H) radicals, namely, H beta and H alpha radicals. As illustrated in FIGS. 13-15, which show the comparison of measured intensity for the hydroxyl, H beta and H alpha radicals were generated in deionized water and deionized water having nanoparticles of $TiO_2$. The increased intensity is indicative of a higher concentration of the radicals, which are attributed to the addition of the catalysts.

Figure 16:
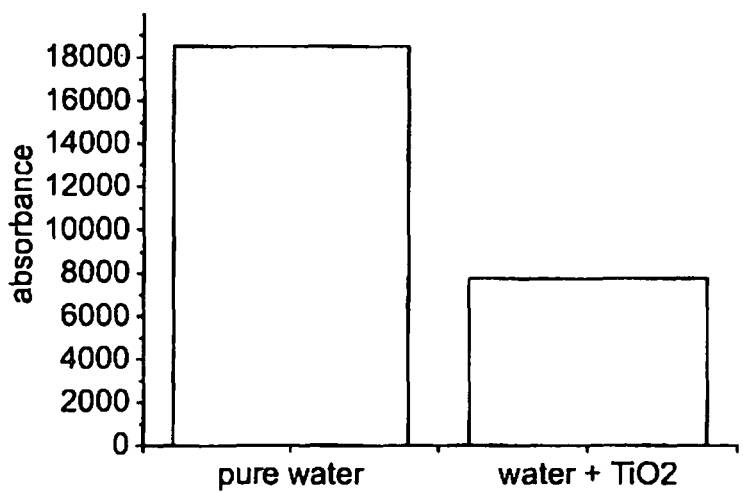
FIG. 16 shows a bar graph of absorbance of methylene blue in deionized water in the presence and in the absence of catalysts according to the present disclosure.

FIG. 16 shows the absorption of methylene blue in pure deionized water and in deionized water including nanoparticles of $TiO_2$. Methylene blue is a common indicator chemical of hydroxyl radicals since methylene blue reacts with hydroxyl radicals, which causes a change in color from blue to clear. The sample with nanoparticles had a lower absorption, indicating a higher reaction ratio with the hydroxyl radicals than the pure deionized water sample. In the pure deionized water sample, the absorption value is higher since a larger amount of methelyne blue remained unreacted due to lower production of the hydroxyl particles due to the lack of the nanoparticles of $TiO_2$.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. In particular, as discussed above this allows the tailoring of the relative populations of plasma species to meet needs for the specific process desired on the workpiece surface or in the volume of the reactive plasma.

What is claimed is:
1. A plasma system for treating a workpiece, comprising:
a plasma device including:
an electrode having an inner surface and an outer surface and formed from a metal alloy; and
a dielectric layer covering the inner and outer surfaces of the electrode and including a distal portion extending distally past a distal end of the electrode by an exposure distance, the dielectric layer being slidable along and relative to the inner and outer surfaces of the electrode to change the exposure distance during treatment of a workpiece;

a liquid source configured to supply a liquid to a workpiece;

an ionizable media source coupled to the plasma device and configured to supply ionizable media thereto; and a power source coupled to the electrode and configured to ignite the ionizable media at the plasma device to form a plasma effluent in the presence of the liquid, whereby the plasma effluent reacts with the liquid to form at least one reactive species that interacts with the workpiece.

2. A plasma system according to claim 1, wherein the metal alloy is selected from the group consisting of an aluminum alloy and a titanium alloy.

3. A plasma system according to claim 2, wherein the dielectric layer is selected from the group consisting of an oxide, a nitride, a native oxide and a native nitride.

4. A plasma system according to claim 1, wherein the liquid is an aqueous solution of a compound selected from the group consisting of salts, bases, acids and reactive gases.

5. A plasma system according to claim 1, wherein the liquid includes catalyst nanoparticles having a volume average diameter from about 0.1 nm to about 1,000 nm.

6. A plasma system according to claim 1, wherein the electrode has a cylindrical tubular shape.

* * * * *